United States Patent
Cipolla et al.

(10) Patent No.: US 9,968,555 B2
(45) Date of Patent: May 15, 2018

(54) LIPOSOMAL FORMULATIONS THAT FORM DRUG NANOCRYSTALS AFTER FREEZE-THAW

(71) Applicant: ARADIGM CORPORATION, Hayward, CA (US)

(72) Inventors: David C. Cipolla, San Ramon, CA (US); Igor Gonda, San Francisco, CA (US)

(73) Assignee: ARADIGM CORPORATION, Hayward, CA (US)

( * ) Notice: Subject to any disclaimer, the term of this patent is extended or adjusted under 35 U.S.C. 154(b) by 618 days.

(21) Appl. No.: 14/619,874

(22) Filed: Feb. 11, 2015

(65) Prior Publication Data
US 2015/0283076 A1 Oct. 8, 2015

Related U.S. Application Data

(60) Provisional application No. 61/976,729, filed on Apr. 8, 2014.

(51) Int. Cl.
| | |
|---|---|
| A61K 9/127 | (2006.01) |
| A61K 47/26 | (2006.01) |
| A61K 31/496 | (2006.01) |
| A61K 9/00 | (2006.01) |
| A61K 45/06 | (2006.01) |

(52) U.S. Cl.
CPC ............ *A61K 9/127* (2013.01); *A61K 9/0078* (2013.01); *A61K 31/496* (2013.01); *A61K 45/06* (2013.01); *A61K 47/26* (2013.01)

(58) Field of Classification Search
CPC ..................................................... A61K 9/127
See application file for complete search history.

(56) References Cited

U.S. PATENT DOCUMENTS

| | | | |
|---|---|---|---|
| 5,902,604 A * | 5/1999 | Zou | A61K 9/1272 264/4.1 |
| 7,244,413 B2 | 7/2007 | Barbera-Guillem | |
| 2002/0102293 A1* | 8/2002 | Sachse | A61K 9/1277 424/450 |
| 2004/0091541 A1 | 5/2004 | Unger | |
| 2005/0214224 A1* | 9/2005 | Weers | A61K 9/0075 424/45 |

(Continued)

FOREIGN PATENT DOCUMENTS

WO  2014052634  4/2014

OTHER PUBLICATIONS

Bruinenberg P., "Safety, tolerability and pharmacokinetics of novel liposomal ciprofloxacin of novel liposomal ciprofloxacin formulations for inhalation in healthy volunteers and in non-cystic bronchiectasis patients", Am. J. Respir. Crit. Care Med. (2010) 181:A3192.

(Continued)

*Primary Examiner* — Gollamudi Kishore
(74) *Attorney, Agent, or Firm* — Karl Bozicevic; Bozicevic, Field & Francis LLP

(57) ABSTRACT

Methods for formulating a liposome comprised of a surfactant and a cryopreservative that can be frozen for long term stability, and upon thawing provides an immediate and sustained release delivery profile. Specific liposome formulations include anti-infectives and delivery of such for treatment of respiratory tract infections and other medical conditions, and devices and formulations used in connection with such are described.

15 Claims, 13 Drawing Sheets

CryoTEM micrograph image of a liposome formulation that forms nanocrystals following freeze-thaw. (scale bar is 100 nm)

(56) References Cited

U.S. PATENT DOCUMENTS

| | | | | |
|---|---|---|---|---|
| 2006/0159739 | A1* | 7/2006 | Lasic | A61K 9/1271 424/450 |
| 2009/0196917 | A1* | 8/2009 | Joguparthi | A61K 9/0019 424/450 |
| 2012/0009253 | A1* | 1/2012 | Fleischer | A61K 9/127 424/450 |
| 2013/0039847 | A1* | 2/2013 | Gessler | A61K 9/127 424/1.11 |
| 2013/0121918 | A1 | 5/2013 | Hong et al. | |
| 2014/0161876 | A1 | 6/2014 | Isoda | |
| 2014/0255472 | A1 | 9/2014 | Geall et al. | |
| 2015/0283076 | A1 | 10/2015 | Cipolla et al. | |
| 2015/0283133 | A1 | 10/2015 | Gonda et al. | |

OTHER PUBLICATIONS

Carter G., "Characterization of biofilm formation by *Mycobacterium avium* strains", J. Med. Microbiol. (2003) 52: 747-52.

Cipolla D., "Liposomal Formulations for Inhalation", Ther. Deliv., (2013) 4, 8, 1047-1072. doi: 10.4155/tde.13.71.

Cipolla D., "Development and Characterization of an In Vitro Release Assay for Liposomal Ciprofloxacin for Inhalation", J. Pharm. Sci., (2014) 103, 1, 314-327. doi: 10.1002/jps.23795.

Lasic DD., "Gelation of liposome interior: A novel method for drug encapsulation", FEBS Lett., (1992) 312:255-258.

Stark B., "Long-term stability of sterically stabilized liposomes by freezing and freeze-drying: Effects of cryoprotectants on structure", Eur. J. Pharm. Sci. 41(2010) 546-555.

Strauss G. "Stabilization of lipid bilayer by sucrose during freezing", PNAS (1986) 83, 2422-2426.

Wolkers WF. "Preservation of dried liposomes in the presence of sugar and phosphate" Biochim. Biphys. Acta. 1661, 125-134.

Yamazaki Y. "The ability to form biofilm influences *Mycobacterium avium* invasion and translocation of bronchial epithelial cells" Cell Microbiol. (2006) 8: 806-14.

Zhigaltsev IV. "Formation of drug-arylsulfonate complexes inside liposomes: A novel approach to improve drug retention" J. Control Rel. 110: 378-386.

Cipolla, et al., "Formation of drug nanocrystals under nanoconfinement afforded by liposomes," Royal Society of Chemistry Advances (Jan. 2016) 6:6223-6233.

Anonymous: "Nanotechnology for Cancer Therapy" CRC Press XP-002772115 (Dec. 19, 2006) 1 page.

Ausborn et al., "The protective effect of free and membrane-bound cryoprotectants during freezing and freeze-drying of liposomes" Journal of Controlled Release (1994) 30:105-116.

Costa et al., "Freeze-Anneal-Thaw Cycling of Unilamellar Liposomes: Effect on Encapsulation Efficiency" Pharm Res (2014) 31:97-103.

* cited by examiner

Figure 1: Drug encapsulation after freeze thaw as a function of the ratio of surfactant to lipids in the liposome
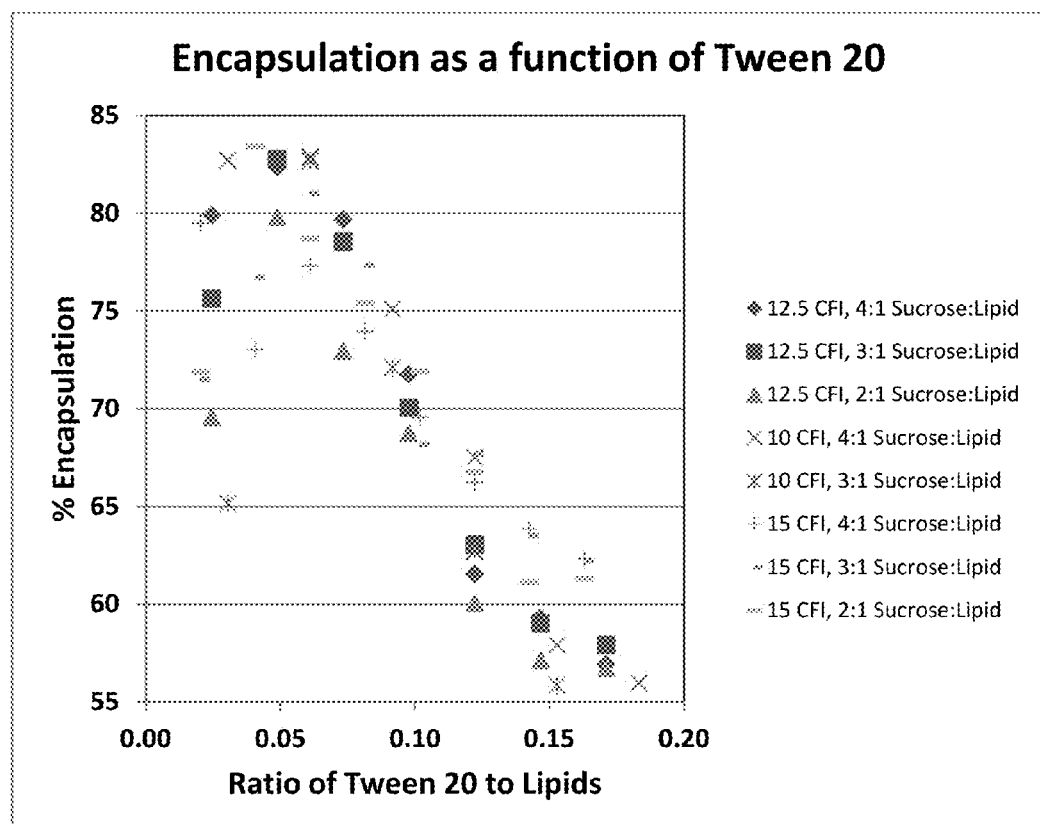

Figure 2: Drug encapsulation after frozen storage for 6 weeks and subsequent thawing as a function of the ratio of surfactant to lipids in the liposome
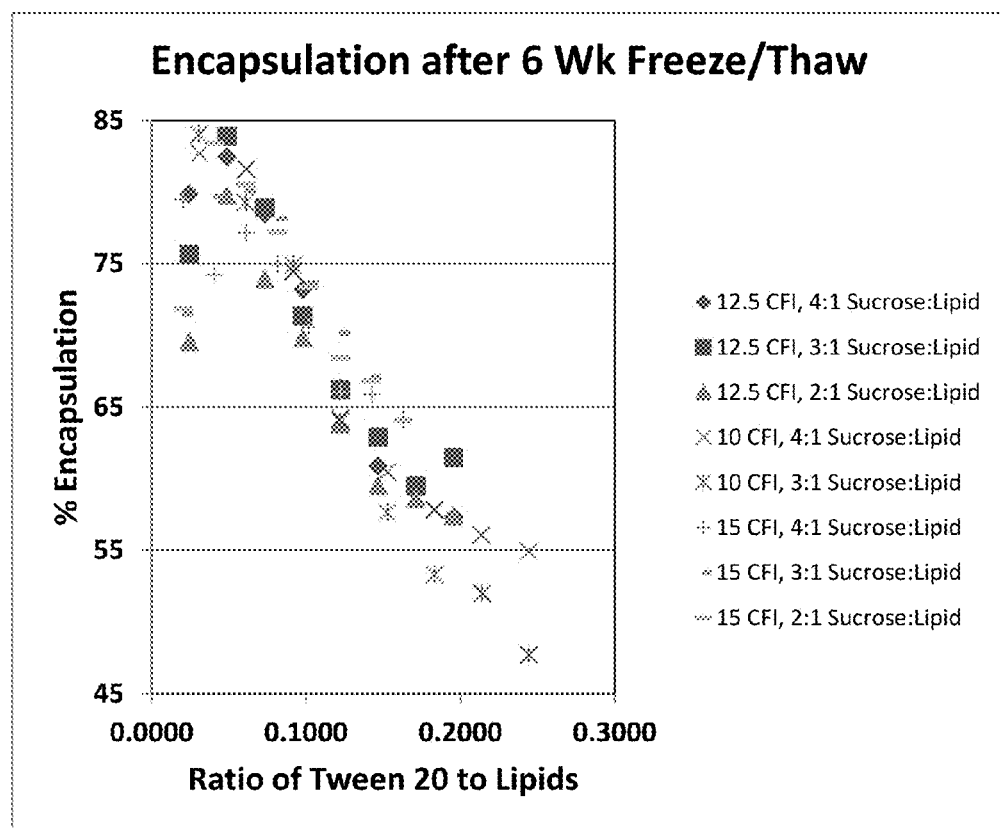

Figure 3: CryoTEM micrograph image of a liposome formulation that forms nanocrystals following freeze-thaw. (scale bar is 100 nm)
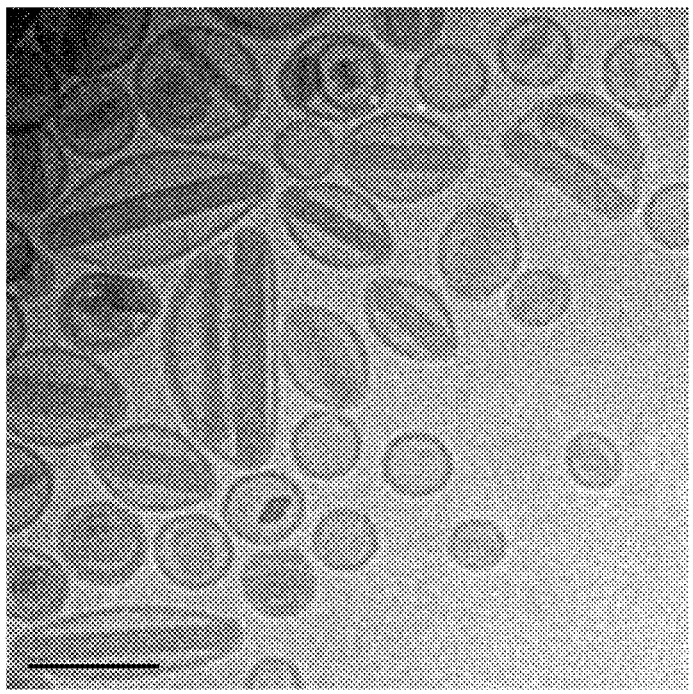

Figure 4: CryoTEM micrograph image of the same liposome formulation prior to freeze-thaw. (scale bar is 100 nm)
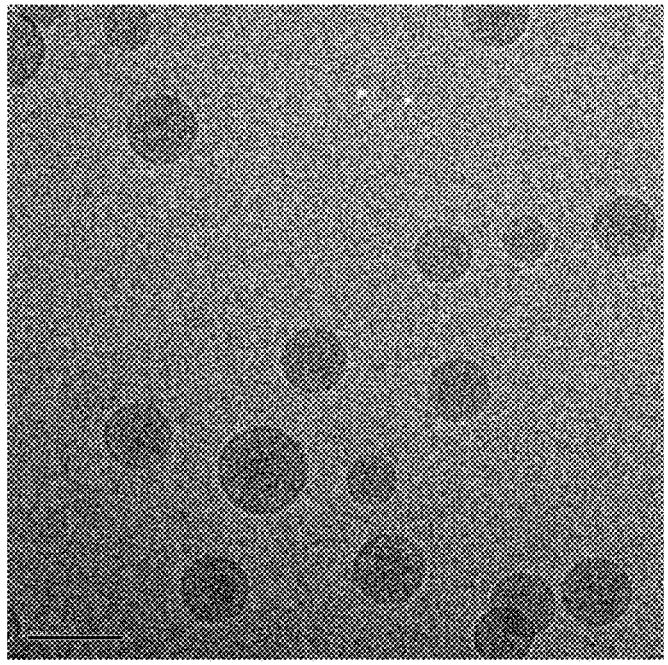

Figure 5: Modified In Vitro Release Profiles (IVR) for Three CFI Formulations after Freeze-thaw:
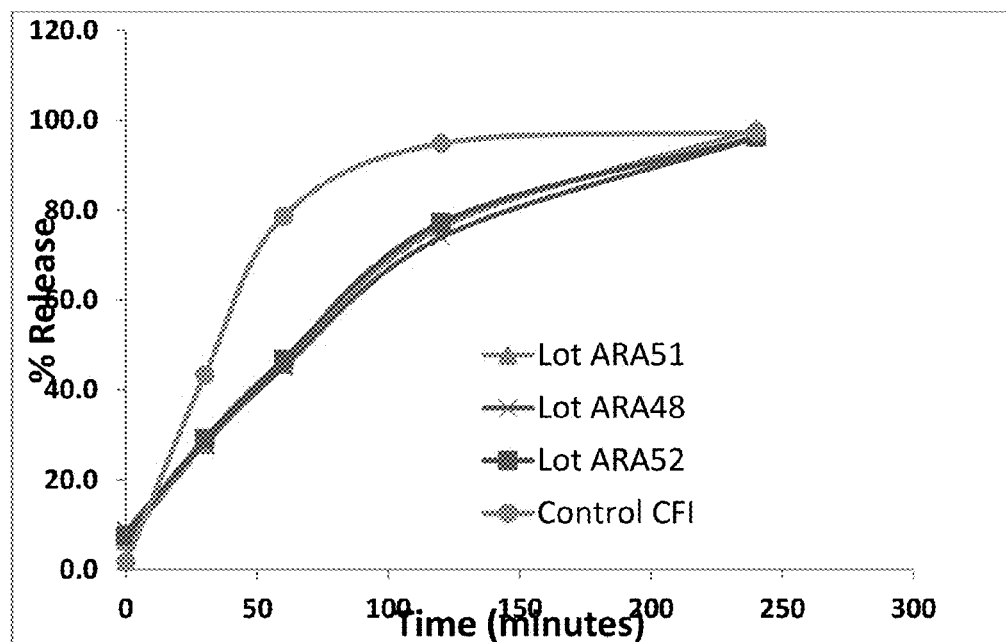

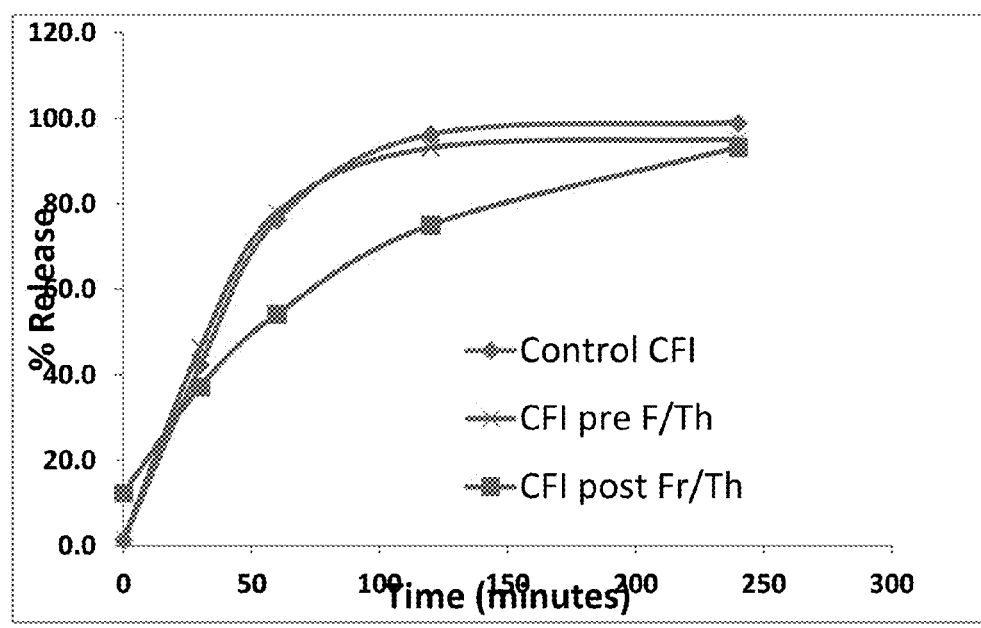
Figure 6: IVR Profiles Before and After Freeze Thaw:

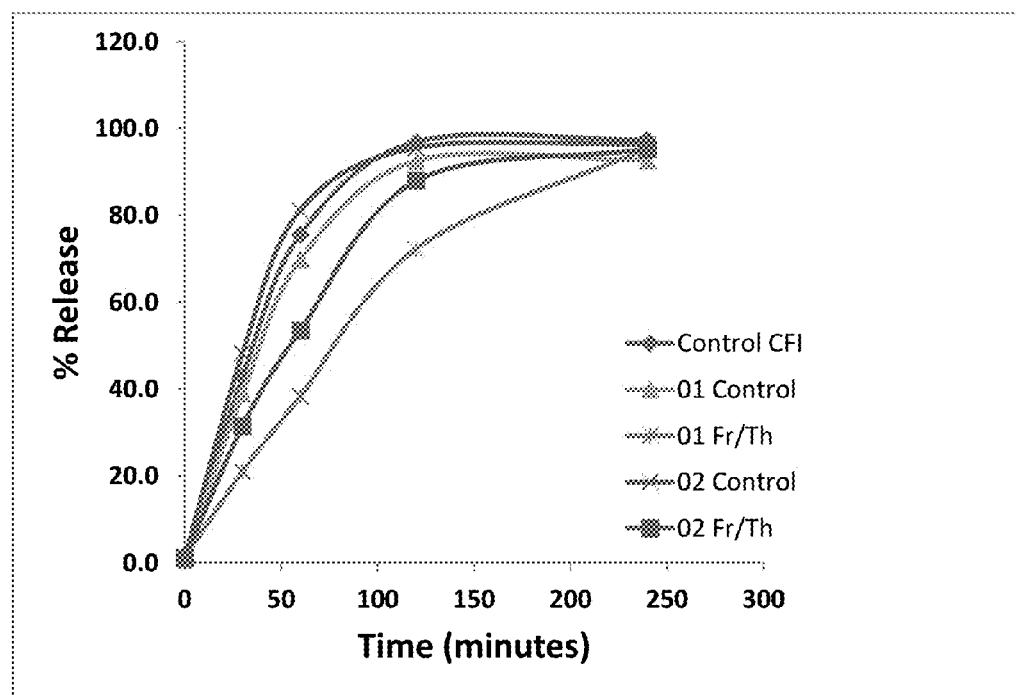
Figure 7: IVR Profiles Before and After Freeze Thaw

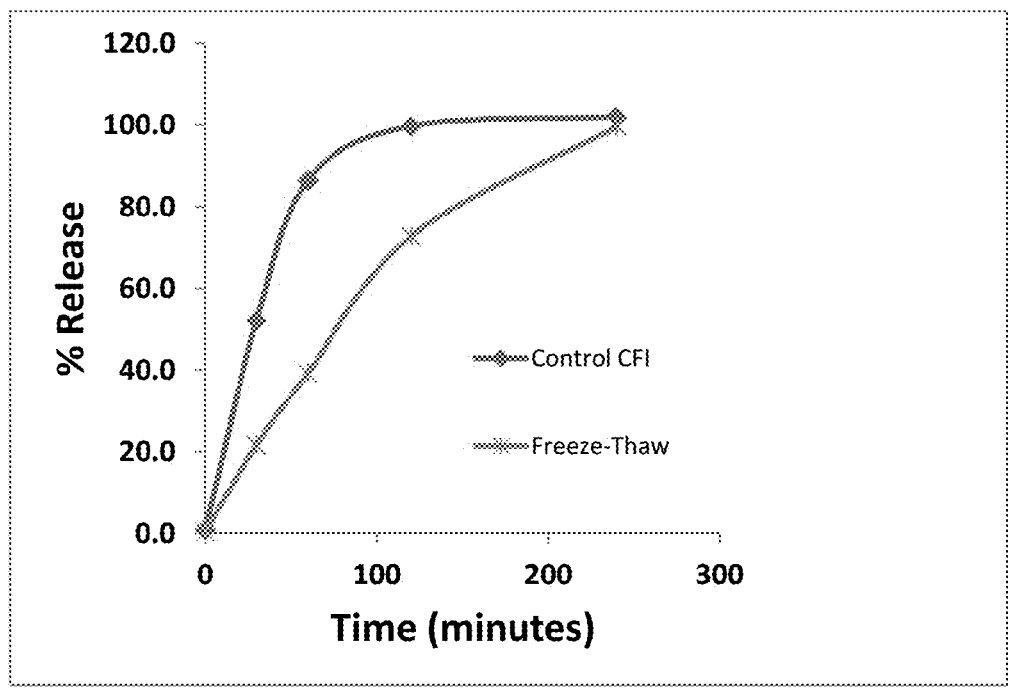
Figure 8: IVR Profiles Before and After Freeze Thaw

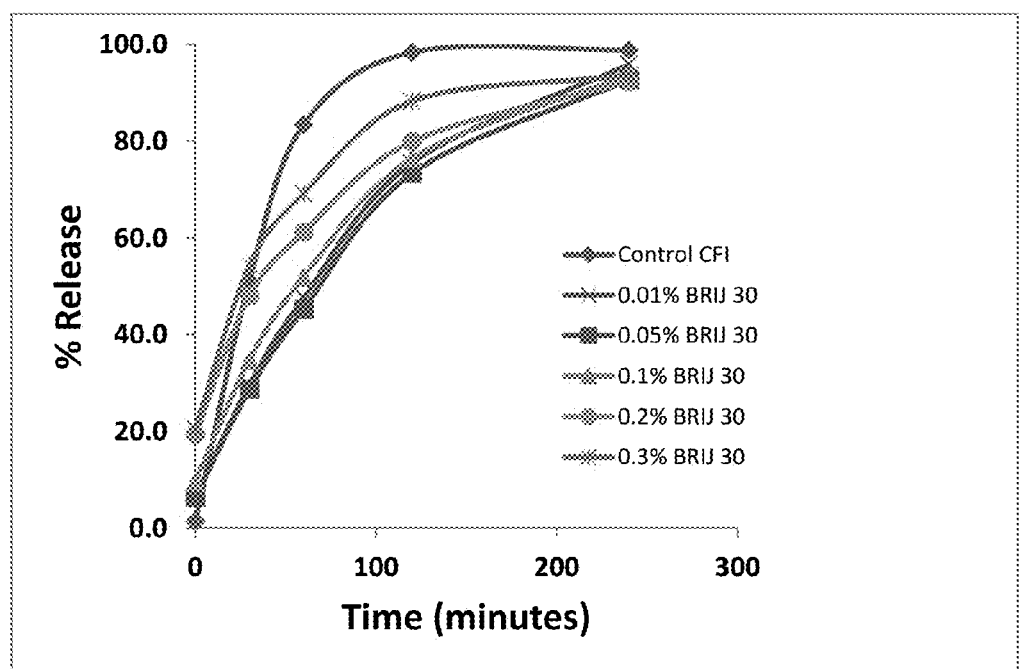
Figure 9: IVR Profiles Before and After Freeze Thaw

Figure 10: CryoTEM micrograph image of a liposome formulation that forms nanocrystals following freeze-thaw. (scale bar is 100 nm)
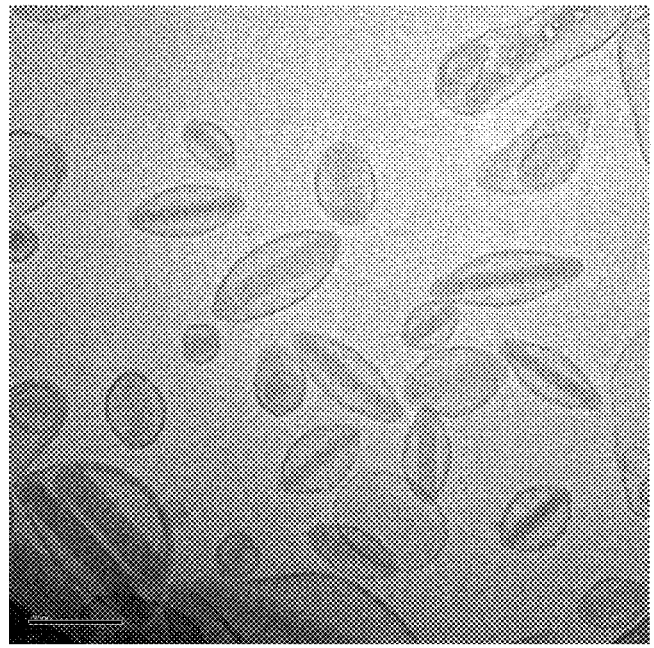

Figure 11: CryoTEM micrograph image of a liposome formulation that forms nanocrystals following freeze-thaw. (scale bar is 100 nm)
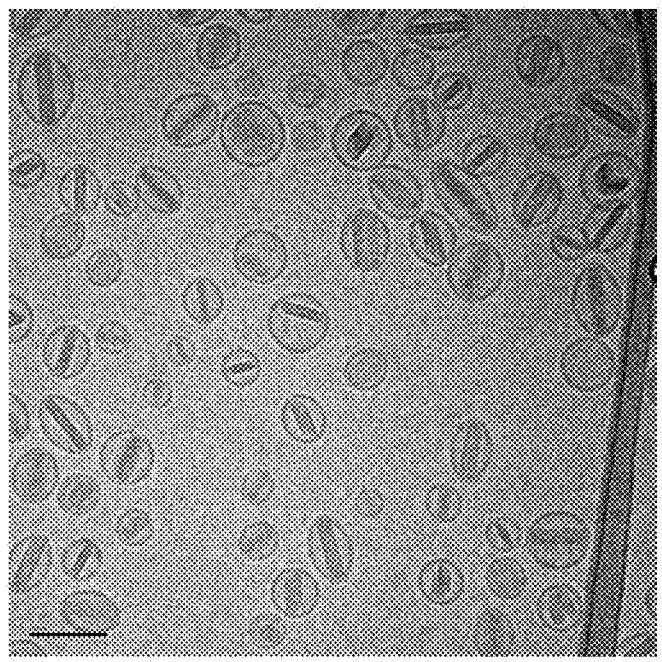

Figure 12: CryoTEM micrograph image of a liposome formulation that forms nanocrystals following freeze-thaw. (scale bar is 100 nm)
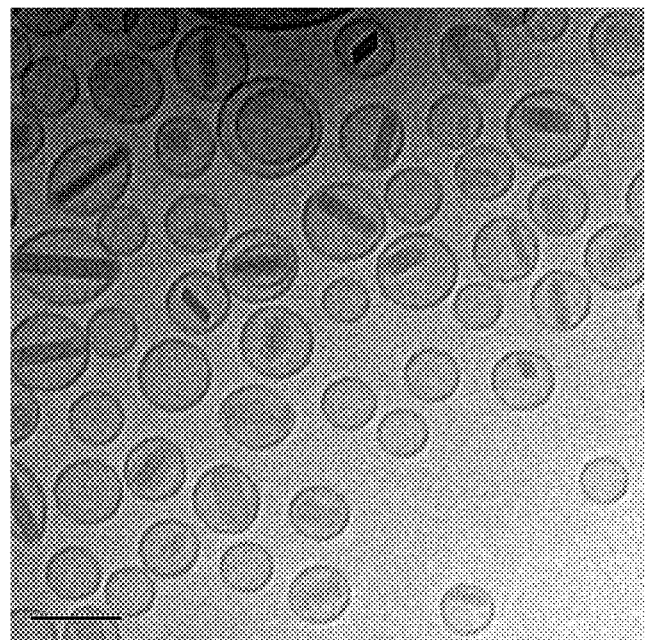

Figure 13: CryoTEM micrograph image of a liposome formulation that forms nanocrystals following freeze-thaw and retains liposome structures with nanocrystals after aerosolization by mesh nebulization. (scale bar is 100 nm)

LIPOSOMAL FORMULATIONS THAT FORM DRUG NANOCRYSTALS AFTER FREEZE-THAW

FIELD OF THE INVENTION

The present invention relates to pharmaceutical compositions such as for treating respiratory tract infections caused by a variety of microorganisms or intracellular pathogens. In particular, the present invention relates to formulations with modified release profiles after freeze-thaw which provide for immediate and sustained release of a drug such as anti-infectives. They can be delivered by a variety of methods. For example, these formulations can be delivered by inhalation for the treatment of cystic fibrosis (CF), non-CF bronchiectasis, COPD, and intracellular lung infections including non tuberculous mycobacteria (NTM), as well as prevention and treatment of bioterrorism infections, particularly those that can be transmitted by inhalation, such as anthrax, tularemia, pneumonic plague, melioidosis and Q-fever.

BACKGROUND OF THE INVENTION

Infections are caused by a variety of microorganisms. Infections which are persistent have a myriad of consequences for the health care community including increased treatment burden and cost, and for the patient in terms of more invasive treatment paradigms and potential for serious illness or even death. It would be beneficial if an improved treatment paradigm were available to provide prophylactic treatment to prevent susceptible patients from acquiring infections as well as increasing the rate or effectiveness of eradicating the infections in patients already infected with the microorganisms.

In particular, cystic fibrosis (CF) is one example of a disease in which patients often acquire persistent or tenacious respiratory tract infections, including *P. aeruginosa* (PA). Another disease which is associated with recurring PA lung infections is non-CF bronchiectasis. A subset of COPD patients also suffers from PA lung infections and many have bronchiectasis.

High rates of colonization and the challenge of managing PA infections in patients with cystic fibrosis (CF) have necessitated a search for safe and effective antibiotics. Currently, inhaled tobramycin, colistin, or aztreonam is the standard of care in CF. Nothing is currently approved for treatment of patients with NTM infections, or for non-CF bronchiectasis patients.

While azithromycin possesses activity against *Staphylococcus aureus, Haemophilus influenzae*, and *Streptococcus pneumoniae*, it has no direct activity against *Pseudomonas aeruginosa, Burkholderia cepacia*, or other gram-negative non-fermenters (Lode H et al., 1996). Tobramycin possesses activity against *P. aeruginosa*; however, the increase in the number of patients with resistant isolates on continuous therapy from ~10% to 80% after 3 months (Smith A L et al., 1989) has led to the intermittent dosing regimen of 28-days-on followed by 28-days-off therapy. The development of a therapeutic regimen that delivers the anti-infective therapy in a continuous fashion, while still inhibiting the emergence of resistant isolates, may provide an improved treatment paradigm. It is noteworthy that chronic PA airway infections remain the primary cause of morbidity and mortality in CF patients. When patients experience pulmonary exacerbations, the use of systemic antipseudomonal therapy, frequently consisting of a β-lactam and an aminoglycoside, may result in clinical improvement and a decrease in bacterial burden. Eradication of the infection, however, is quite rare.

In CF airways, PA initially has a non-mucoid phenotype, but ultimately produces mucoid exopolysaccharide and organizes into a biofilm, which indicates the airway infection has progressed from acute to chronic. Bacteria in biofilms are very slow growing due to an anaerobic environment and are inherently resistant to antimicrobial agents, since sessile cells are much less susceptible than cells growing planktonically. It has been reported that biofilm cells are at least 500 times more resistant to antibacterial agents (Costerton J W et al., 1995). Thus, the transition to the mucoid phenotype and production of a biofilm contribute to the persistence of PA in CF patients with chronic infection by protecting the bacteria from host defenses and interfering with the delivery of antibiotics to the bacterial cell. Although much effort has been made to improve the care and treatment of individuals with CF, and the average lifespan has increased, the median age of survival for people with CF is only to the late 30s (CF Foundation web site, 2006).

Pulmonary infections from non-tuberculous mycobacteria (NTM) are also notoriously difficult to treat. They exist in the lungs in various forms, including within macrophages and in biofilms. These locations are particularly difficult to access with antibiotics. Furthermore, the NTM may be either in a dormant (termed sessile), or a replicating phase, and an effective antibiotic treatment would target both phases.

Lung infection from *Mycobacterium avium* subsp *hominissuis* (hereafter referred as *M. avium*) and *Mycobacterium abscessus* is a significant health care issue and there are major limitations with current therapies. The incidence of pulmonary infections by non-TB mycobacteria (NTM) is increasing (Adjemian et al., 2012; Prevots et al, 2010), specifically with *M. avium* and *M. abscessus* (Inderlied et al, 1993). About 80% of NTM in US is associated with *M. avium* (Adjemian et al., 2012; Prevots et al, 2010). *M. abscessus*, which is amongst the most virulent types, ranks second in incidence (Prevots et al, 2010). Diseases caused by both mycobacteria are common in patients with chronic lung conditions, e.g., emphysema, cystic fibrosis, and bronchiectasis (Yeager and Raleigh, 1973). They may also give rise to severe respiratory diseases, e.g., bronchiectasis (Fowler et al, 2006). The infections are from environmental sources and cause progressive compromising of the lung.

Current therapy often fails on efficacy or is associated with significant side-effects. *M. avium* infection is usually treated with systemic therapy with a macrolide (clarithromycin) or an azalide (azithromycin) in combination with ethambutol and amikacin. Oral or IV quinolones, such as ciprofloxacin and moxifloxacin, can be used in association with other compounds (Yeager and Raleigh, 1973), but higher intracellular drug levels need to be achieved for maximal efficacy. Oral ciprofloxacin has clinical efficacy against *M. avium* only when administered in combination with a macrolide or an aminoglycoside (Shafran et al 1996; de Lalla et al, 1992; Chiu et al, 1990). Studies in vitro and in mouse suggest that the limited activity of oral ciprofloxacin alone is related to the inability of ciprofloxacin to achieve bactericidal concentrations at the site of infection (Inderlied et al, 1989); the minimum inhibitory concentration (MIC) of 5 µg/ml versus the clinical serum Cmax of 4 µg/ml explains the limited efficacy in experimental models and in humans (Inderlied et al, 1989). *M. abscessus* is often resistant to clarithromycin. IV aminoglycosides or imipenem need to be applied, which often are the only available therapeutic alternatives, and these carry the potential for serious side-effects, as well as the trauma and cost associated with IV administration. Clofazimine, linezolid, and cefoxitin are also sometimes prescribed, but toxicity and/or the need for IV administration limit the use of these compounds. Thus, the available therapies have significant deficiencies and improved approaches are needed.

Recent studies also showed that both *M. avium* and *M. abscessus* infections are associated with significant biofilm formation (Bermudez et al, 2008; Carter et al, 2003): deletion of biofilm-associated genes in *M. avium* had impact on the ability of the bacterium to form biofilm and to cause pulmonary infection in an experimental animal model (Yamazaki et al, 2006).

Deliberate release of microbial agents in the form of mists or aerosols poses a serious bioterrorism threat. More effective methods for prevention and treatment of bioterrorism infections, particularly those that can be transmitted by inhalation, such as anthrax, tularemia, pneumonic plague, melioidosis and Q-fever, are desirable. Their stock piling in the form of frozen formulations that could be thawed to form medicines with desirable properties would be particularly attractive.

Thus, a continuing need exists for improved formulations of anti-infectives, especially for administration by inhalation. The present invention addresses this need.

Ciprofloxacin is a fluoroquinolone antibiotic that is indicated for the treatment of lower respiratory tract infections due to PA, which is common in patients with cystic fibrosis. Ciprofloxacin is broad spectrum and, in addition to PA, is active against several other types of gram-negative and gram-positive bacteria. It acts by inhibition of topoisomerase II (DNA gyrase) and topoisomerase IV, which are enzymes required for bacterial replication, transcription, repair, and recombination. This mechanism of action is different from that for penicillins, cephalosporins, aminoglycosides, macrolides, and tetracyclines, and therefore bacteria resistant to these classes of drugs may be susceptible to ciprofloxacin. Thus, CF patients who have developed resistance to the aminoglycoside tobramycin can likely still be treated with ciprofloxacin. There is no known cross-resistance between ciprofloxacin and other classes of antimicrobials.

Despite its attractive antimicrobial properties, ciprofloxacin does produce bothersome side effects, such as gastrointestinal tract (GIT) intolerance (vomiting, diarrhea, abdominal discomfort), as well as dizziness, insomnia, irritability and increased levels of anxiety. There is a clear need for improved treatment regimes that can be used chronically, without resulting in these debilitating side effects.

Delivering ciprofloxacin as an inhaled aerosol has the potential to address these concerns by compartmentalizing the delivery and action of the drug in the respiratory tract, which is the primary site of infection.

Currently there is no aerosolized form of ciprofloxacin with regulatory approval for human use, capable of targeting antibiotic delivery direct to the area of primary infection in the respiratory tract. In part this is because the poor solubility and bitterness of the drug have inhibited development of a formulation suitable for inhalation (Barker et al, 2000). Furthermore, the tissue distribution of ciprofloxacin is so rapid that the drug residence time in the lung is too short to provide additional therapeutic benefit over drug administered by oral or IV routes (Bergogne-Bérézin E, 1993).

The therapeutic properties of many drugs are improved by incorporation into liposomes. Phospholipid vehicles as drug delivery systems were rediscovered as "liposomes" in 1965 (Bangham et al., 1965). The general term "liposome" covers a variety of structures, but all consist of one or more lipid bilayers enclosing an aqueous space in which hydrophilic drugs, such as ciprofloxacin, can be encapsulated. Liposome encapsulation improves biopharmaceutical characteristics through a number of mechanisms including altered drug pharmacokinetics and biodistribution, sustained drug release from the carrier, enhanced delivery to disease sites, and protection of the active drug species from degradation. Liposome formulations of the anticancer agents doxorubicin (Myocet®/Evacet®, Doxyl®/Caelyx®), daunorubicin (DaunoXome®) the anti-fungal agent amphotericin B (Abelcet®, AmBisome®, Amphotec®) and a benzoporphyrin (Visudyne®) are examples of successful products introduced into the US, European and Japanese markets over the last two decades. Recently a liposomal formulation of vincristine (Marqibo®) was approved for an oncology indication. The proven safety and efficacy of lipid-based carriers make them attractive candidates for the formulation of pharmaceuticals.

Delivery of liposome formulations by inhalation offers many attractive features, providing that the liposome formulation is stable to the aerosolization process (Niven and Schreier, 1990; Cipolla et al, 2013). Therefore, in comparison to the current ciprofloxacin formulations, a liposomal ciprofloxacin aerosol formulation should offer several benefits: 1) higher drug concentrations, 2) increased drug residence time via sustained release at the site of infection, 3) decreased side effects, 4) increased palatability, 5) better penetration into the bacteria, and 6) better penetration into the cells infected by bacteria. It has previously been shown that inhalation of liposome-encapsulated fluoroquinolone antibiotics may be effective in treatment of lung infections. In a mouse model of *F. tularensis* liposomal encapsulated fluoroquinolone antibiotics were shown to be superior to the free or unencapsulated fluoroquinolone by increasing survival (CA2,215,716, CA2,174,803, and CA2,101,241).

U.S. Pat. Nos. 8,071,127, 8,119,156, 8,268,347 and 8,414,915 describe an aerosol consisting of inhaled droplets or particles. The droplets or particles comprise a free drug (e.g., an anti-infective compound) in which drug is not encapsulated and which may be ciprofloxacin. The particles further comprise liposomes which encapsulate a drug such as an anti-infective compound which also may be ciprofloxin. The free and liposome encapsulated drug are included within a pharmaceutically acceptable excipient which is formulated for aerosolized delivery. The particles may further include an additional therapeutic agent which may be free and/or in liposomes and which can be any pharmaceutically active drug which is different from the first drug. The liposomes in these patents are unilamellar vesicles (average particle size 75-120 nm). Ciprofloxacin is released slowly from the liposomes with a half-life of about 10 hours in the lung (Bruinenberg et al, 2010 b), which allows for once-a-day dosing.

Further, studies with a variety of liposome compositions in in vitro and murine infection models showed that liposomal ciprofloxacin is effective against several intracellular pathogens, including *M. avium*. Inhaled liposomal ciprofloxacin is also effective in treating *Pseudomonas aeruginosa* (PA) lung infections in patients (Bilton et al, 2009 a, b, 2010, 2011; Bruinenberg et al, 2008, 2009, 2010 a, b, c, d, 2011; Serisier et al, 2013). Compared to approved doses of oral and IV ciprofloxacin, liposomal ciprofloxacin formulations delivered by inhalation achieve much greater concentrations in the respiratory tract mucosa and within macrophages with resulting improvement of clinical efficacy: 2 hours post-inhalation of a therapeutic dose of such liposomal ciprofloxacin in patients, the concentration of ciprofloxacin in the sputum exceeded 200 µg/ml, and even 20 hours later (2 hours prior to the next dose), the concentration was >20 µg/ml, well above the minimum inhibitory concentration above for resistant mycobacteria (breakpoint of ~4 µg/ml (Bruinenberg 2010b). Since the liposomes containing ciprofloxacin are avidly ingested by macrophages, the ciprofloxacin is brought into close proximity to the intracellular pathogens, thus further increasing anti-mycobacterial concentration and thus should lead to improved efficacy of the inhaled liposomal formulation compared to other forms of ciprofloxacin. We therefore believe that even highly resistant NTM may be suppressed with such inhaled liposomal ciprofloxacin formulations. This is significant because *M. avium* and *M. abscessus* resistance to antibiotics is common due to long-term use of systemic antibiotics in these patients. The clinical experience with PA also shows that there is no apparent emergence of resistance following inhaled liposomal ciprofloxacin therapy: in fact, even those patients who also had resistant strains initially, responded well to therapy. This is likely due to the presence of sustained overwhelming concentrations of ciprofloxacin. Furthermore, the experience with other antipseudomonal drugs tobramycin and colistimethate in cystic fibrosis is that even patients with resistant strains of PA respond clinically well to the inhaled form of the drugs (Fiel, 2008).

A few in vitro studies have demonstrated that liposomal ciprofloxacin is efficacious against intracellular pathogens: *M. avium* infection: 1) In human peripheral blood monocytes/macrophages, liposomal ciprofloxacin tested over concentrations from 0.1 to 5 µg/ml caused concentration-related reductions in intracellular *M. avium-M. intracellulare* complex (MAC) colony forming units (CFU) compared to free drug at the same concentrations (Majumdar et al, 1992); 2) In a murine macrophage-like cell line J774, liposomal ciprofloxacin decreased the levels of cell associated *M. avium* up to 43-fold and these reductions were greater than for free ciprofloxacin (Oh et al, 1995).

Once *M. avium* or *M. abscessus* infect monocytes/macrophages, the infection can then spread to the lungs, liver, spleen, lymph nodes, bone marrow, and blood. There are no published studies on the efficacy of liposomal ciprofloxacin against *M. avium* or *M. abscessus* in animal models.

Several in vivo studies have demonstrated that liposomal ciprofloxacin is efficacious against the intracellular pathogen, *F. tularensis*: Efficacy of liposomal ciprofloxacin delivered to the lungs by inhalation or intranasal instillation against inhalational tularemia (*F. tularensis* LVS and SCHU S4) in mice, was demonstrated with as little as a single dose of liposomal ciprofloxacin providing 100% protection post-exposure, and even effective post-exposure treatment for animals that already had significant systemic infection (Blanchard et al, 2006; Di Ninno et al, 1993; Conley et al, 1997; Hamblin et al, 2011; Wong et al, 1996). The studies also found that inhaled liposomal ciprofloxacin was superior to both inhaled and oral unencapsulated ciprofloxacin.

In contrast, a) free ciprofloxacin was inferior to liposomal ciprofloxacin in macrophage models of mycobacterial infections (Majumdar et al, 1992; Oh et al, 1995); b) free ciprofloxacin alone delivered to the lungs had inferior efficacy to free ciprofloxacin when tested in murine models of *F. tularensis* infection (Conley et al, 1997; Wong et al, 1996), as it is rapidly absorbed into the blood stream. A formulation made up of both free and liposomal ciprofloxacin combines the potential advantages of an initial transient high concentration of free ciprofloxacin to increase Cmax in the lungs, followed by the slow release of ciprofloxacin from the liposomal component, as demonstrated in BE (Cipolla et al, 2011; Serisier et al, 2013). The free ciprofloxacin component also has a desirable immunomodulatory effect (U.S. Pat. Nos. 8,071,127, 8,119,156, 8,268,347 and 8,414,915).

Further, liposomal ciprofloxacin injected parenterally activates macrophages, resulting in increased phagocytosis, nitric oxide production, and intracellular microbial killing even at sub-inhibitory concentrations, perhaps via immuno-stimulatory effects (Wong et al, 2000). The ciprofloxacin-loaded macrophages may migrate from the lungs into the lymphatics to treat infections in the liver, spleen, and bone marrow—as suggested by the systemic effects of pulmonary-delivered CFI in tularemia (Di Ninno et al, 1993; Conley et al, 1997; Hamblin et al, 2011, Wong et al, 1996). Liposome-encapsulated antibiotics are also known to better penetrate bacterial films in the lungs (Meers et al, 2008). The anti-mycobacterial and immunomodulatory effects of the new formulations delivered to the lungs, may therefore provide a better alternative to the existing treatments for patients infected with *M. avium* or *M. abscessus*, or provide an adjunct for incremental improvements.

A pharmacokinetic study of liposomal ciprofloxacin demonstrated high uptake by alveolar macrophages in animals, which is presumably the reason for the highly effective post-exposure prophylaxis and treatment of inhalational tularemia in mice. Although the plasma levels of ciprofloxacin were low following respiratory tract administration of the liposomal ciprofloxacin, a reduction of the tularemia infection from the liver, spleen, tracheobronchial lymph nodes, as well as the lungs, was observed suggesting that the alveolar macrophages loaded with liposomal ciprofloxacin migrate from the lungs via lymph into the liver, spleen and lymph nodes (Conley et al, 1997).

It would be valuable to be able to prolong the shelf life of liposomally encapsulated antibiotics. However, such formulations, such as liposomal ciprofloxacin formulations, are notoriously sensitive to freeze-thaw. For example, after freeze-thaw of the liposomal ciprofloxacin formulations described above, agglomerates of lipids are observed indicating that many of the liposomes do not retain their integrity in response to the stress of freeze-thaw. These thawed formulations certainly could not be effectively used, e.g., as aerosolized due to the physical agglomerates.

It would be ideal to identify a liposome formulation that retains its stability and integrity after freeze-thaw. A frozen formulation would have a longer shelf-life than a refrigerated or room-temperature formulation due to the reduction in mobility of water and the other constituents resulting in a reduction in the rate of the degradation processes (e.g., lipid hydrolysis). There has been extensive literature describing the challenges of freezing liposomes and maintaining liposome integrity following freeze-thaw. Cryoprotectants such as dimethylsulfoxide, glycerol, quaternary amines and carbohydrates have shown promise (Wolkers et al., 2004). It is also well-established that sugars can stabilize phospholipid vesicles during freezing and this stabilization requires direct interaction between sugar and the phospholipid head group (Strauss et al, 1986; Crowe et al, 1988; Izutsu et al, 2011; Stark et al, 2010, Siow et al, 2007; Siow et al, 2008). The addition of sugar, e.g. polyols, to both the internal liposomal fluid and extraliposomal fluid can improve the robustness of liposomes to freeze-thaw and help to maintain liposome integrity. However, not all liposome formulations are fully protected by sugars and in many cases there will be a proportion of vesicles which lose their integrity completely, and others which agglomerate leading to an increase in vesicle size. These events are also associated with loss of encapsulated drug (Strauss et al, 1986; Crowe et al, 1988; Izutsu et al, 2011; Stark et al, 2010, Siow et al, 2007; Siow et al, 2008).

The ability to modify beneficially the properties of the liposome formulation following freeze-thaw has also not been anticipated. Certainly, it is most likely to degrade the liposomes following freeze-thaw, such that the integrity of the liposomes is compromised. However, there have been no published reports of retention of liposome integrity following freeze thaw while simultaneously modifying the drug encapsulation and drug release properties in a beneficial way.

In addition, there have been no reported examples of liposomes containing drug nanocrystals following freeze-thaw. The presence of drug in the form of nanocrystals within the liposomes would have the potential to alter the release properties of the drug, as there are now two factors or constraints affecting the rate of release; i.e., the liposome membrane is one barrier and the requirement for dissolution of the drug from the crystal form prior to transport through the lipid bilayer is the second. Modifying the size and shape of the crystals in the liposomes will allow the release rate to be further adjusted. The size and shape of the crystals can be adjusted by changing the proportions of excipients in the formulation, i.e., increasing or decreasing the concentration of the drug, liposomal lipids, cryopreservative and surfactant. The presence of drug nanocrystals within the liposomes has the potential to improve other properties of the formulation, including its stability characteristics. These modifications in total may improve the therapeutic effect of the liposome formulation or allow for greater convenience in administration profile; e.g., a reduction in the frequency of administration. The improved administration profile could lead to greater patient compliance and thus increased efficacy. The absence of peaks of drug concentration due to slower dissolution and release could also reduce or eliminate undesirable adverse effects with drug crystals that dissolve slowly.

Another opportunity is to create an immediate release profile that is combined with the sustained release profile. After thawing the formulation there may be a proportion of drug which is released from the liposomes and so becomes immediately available upon inhalation. This proportion of "free drug" can be adjusted to between 1 and 60%, or 10 and 50%, or 20 to 40% by adjusting the proportions of excipients in the formulation, i.e., increasing or decreasing the concentration of cryopreservative and/or surfactant. The cryopreservatives may include polyols, sugars, including sucrose, trehalose, lactose, mannital, etc. Surfactants may include non-ionic surfactants including the polysorbates such as polysorbate 20 (also called tween 20). The cryopreservatives may be present either on the inside (intraliposomally) of the liposomes, and on the outside of the liposomes (extraliposomally), or both.

There have been a number of liposomal formulations that contain drug in a precipitated, gel or crystalline form within the liposomes, but all of these drug precipitates are created during the initial drug loading process. For example there are reports of crystallized doxorubicin (Lasic et al, 1992; Lasic et al, 1995; Li et al, 1998), topotecan (Abraham et al, 2004) and vinorelbine (Zhigaltsev et al. 2006) in liposomes after ion/pH gradient loading (Drummond et al, 2008). There have been no reports of liposomes containing encapsulated drug wherein some of the drug forms drug crystals following freeze-thaw.

SUMMARY OF THE INVENTION

A formulation is disclosed which is comprised of liposomes which liposomes are comprised of a lipid bilayer which surrounds a pharmaceutically active drug which drug is comprised of nanocrystals which have dimensions of 200 nanometers or less, 100 nanometers or less, 50 nanometers or less, 10 nanometers or less on 1 or more dimensions of the crystals. The bilayer may be comprised of a cryopreservative which may be a polyol such as trehalose or sucrose and further comprised of a surfactant which may be a non-ionic detergent such as polysorbate 20 or BRIJ 30. The drug may be an anti-infective agent such as ciprofloxacin.

The invention further includes the formulation of the invention as produced by a particular method whereby the drug such as ciprofloxacin is dissolved in an aqueous solution at a concentration in a range of 10 mg/mL or more, 25 mg/mL or more, 50 mg/mL or more, 100 mg/mL or more, 200 mg/mL or more and encapsulated into a lipid bilayer of liposomes. The liposomes are then included within a solution which may, include an anti-infective which may be the same or different from the anti-infective compound encapsulated within the liposomes and as such may be ciprofloxacin. The formulation is frozen such as being frozen at very low temperatures in the range of −20° C. to −80° C. The frozen formulation may be maintained frozen over long periods of time for storage such as one week or more, one month or more, one year or more or may be immediately rethawed for use. Upon rethawing, drug inside of the liposomes forms nanocrystals. Upon administration the drug dissolved in the solvent carrier surrounding the liposomes provides for immediate release of drug followed by a drug being released when the liposomes dissolve in the lung followed by an additional release of drug when the nanocrystals dissolve. The formulation provides for controlled release of an anti-infective drug such as ciprofloxacin over a long period of time in the lungs thereby making it possible to effectively eradicate infections which occur as a biofilm.

One aspect of the invention is a formulation with a specific release profile wherein the release profile is modified after freeze-thaw. This formulation may be administered in a variety of ways. For example, it can be subsequently aerosolized to create inhalable droplets or particles with a modified and/or predetermined release profile. The droplets or particles comprise a free drug (e.g., an anti-infective compound) in which drug is not encapsulated and which may be ciprofloxacin. The particles further comprise a liposome which encapsulates a drug such as an anti-infective compound which also may be ciprofloxacin and a proportion of the encapsulated drug is present as nanocrystals within the liposomes. The shape and length of the nanocrystals inside the liposomes can be selected by incorporation of specific cryopreservatives, and additionally surfactant, at selected concentrations which are elaborated in the examples. The free and liposome encapsulated drug are included within a pharmaceutically acceptable excipient which is formulated for aerosolized delivery. The particles may further include a second therapeutic agent which may be free and/or in a liposome and which can be any pharmaceutically active drug different from the first drug.

The freezing can be done at a variety of freezing rates, and freezing temperatures. For example, the sample can be frozen rapidly using liquid nitrogen and then stored in a freezer at −20° C., or −50° C., or −80° C. or another temperature below 0° C. The sample to be frozen could also be placed directly into a freezer, for example, a −20° C., or −50° C., or −80° C. freezer, and allowed to freeze at a slow or fast freezing rate, dependent upon the design of the freezer. The freezing rate will also depend upon the volume of the sample to be frozen, and the heat transfer properties of its storage container, and this invention anticipates a range in volumes from 50 µL up to 50 or 100 L or more. More preferably the volume will be between 1 mL and 10 mL. The container material can also vary in composition from glass to plastic, to metal, or combinations thereof.

The formulation and the resulting particles created when the formulation is aerosolized are comprised of a pharmaceutically acceptable carrier, a cryopreservative, free drug, and drug encapsulated within liposomes in the form of drug nanocrystals. In some situations the pharmaceutically acceptable carrier can be completely eliminated such as when the free drug is in a liquid state. However, the carrier is generally necessary to provide a solvent for the free drug and that solvent may be water, ethanol, a combination of water and ethanol or other useful solvents that are not harmful to humans and animals. The percentage of solvent in the formulation may vary from 0% to 90%, 1% to 50%, 2% to 25% by weight but is generally kept at a level which is sufficiently high to maintain the drug in solution at the pH of the formulation. That level will vary from drug to drug and vary as the pH varies. The carrier can be present in the formulation in an amount by weight of 10%, 20%, 30%, 40%, 50%, 60% etc. or more or any incremental amounts there in between.

The formulation includes the drug in two different forms. First, the drug is in a free form which is either liquid or dissolved in a solvent. Second, the drug is encapsulated in liposomes. The ratio of the free drug to the drug encapsulated in liposomes can vary. Generally, the free drug makes up 0%, 5%, 10%, 20%, 30%, etc. up to 80% of the formulation by weight. The drug present within the liposome makes up the remaining percentage of drug present in the formulation. Thus, drug present in the liposomes can be present in a weight amount of from 20% up to 100% of the total drug present in the formulation. A portion of the drug present in the liposomes is in the form of drug nanocrystals.

The formulation may have a pH of 6.0±20%. In some aspects of the invention the formulation is prepared at a relatively low pH such as 3.0, 3.5, 4.0, 4.5, 5.0, or 5.5.

The formulation includes liposomes which have the encapsulated pharmaceutically active drug, for which the liposomes are designed to provide for controlled release of the drug. Controlled release of this aspect of the invention indicates that the drug may be released in an amount of about 0.1% to 100% per hour over a period of time of 1-24 hours or 0.5% to 20% per hour over a period of time of 1-12 hours, or alternatively, releases about 2% to 10% per hour over a period of time of about 1 to 6 hours. Incremental amounts in terms of the percentage of the drug and the number of hours which are between the ranges provided above in half percentage amounts and half hour amounts and other incremental amounts are intended to be encompassed by the present invention.

One aspect of the invention is a formulation comprising liposomes which are delivered via an aerosol to the lungs of a human patient, the liposomes comprising free and encapsulated ciprofloxacin or other anti-infective agent. The liposomes may be unilamellar or multilamellar, and may be bioadhesive, containing a molecule such as hyaluronic acid. At least one therapeutic agent in addition to the free and liposome-encapsulated anti-infective may also be included in the composition. That therapeutic agent may be free drug or encapsulated drug present with a pharmaceutically acceptable carrier useful for direct inhalation into human lungs.

The other drugs may include enzymes to reduce the viscoelasticity of the mucus such as DNase or other mucolytic agents, chemicals to upregulate the chloride ion channel or increase flow of ions across the cells, including lantibiotics such as duramycin, agents to promote hydration or mucociliary clearance including epithelial sodium channel (ENaC) inhibitors or P2Y2 agonists such as denufosol, elastase inhibitors including Alpha-1 antitrypsin (AAT), bronchodilators, steroids, N-acetylcysteine, interferon gamma, interferon alpha, agents that enhance the activity of the antibiotic against biofilm bacteria such as sodium salicylate (Polonio R E et al., 2001), or antibiotics known to those skilled in the art. Inflammation and constriction of the airways are also associated with cystic fibrosis and its treatment. Accordingly, bronchodilators, such as $\beta_2$-adrenergic receptor agonists and antimuscarinics, and anti-inflammatory agents, including inhaled corticosteroids, non-steroidal anti-inflammatories, leukotriene receptor antagonists or synthesis inhibitors, and others, may also be combined with an anti-infective.

A further aspect of the invention is a method for treating cystic fibrosis in a patient, the method comprising administering a formulation comprising the anti-infective; e.g., ciprofloxacin, encapsulated in liposomes to the patient. The formulation is preferably administered by inhalation to the patient.

Another aspect of the invention is a method for treating intracellular lung infections, in particular NTM infections. The presence of drug nanocrystals in the liposomes following freeze-thaw is associated with a delayed release profile. This delayed release profile provides another benefit of allowing more time for uptake of the liposomes by the infected cells, in particular the alveolar macrophages, thus increasing the amount of active drug delivered to the intracellular infections. Another benefit is that once the infected cells take up the liposomes containing the drug nanocrystals, the drug release rate inside the cells may be extended in duration, thus improving the efficacy of treatment.

According to another aspect of the present invention, a formulation comprising both a free and encapsulated anti-infective provides an initially high therapeutic level of the anti-infective in the lungs to eradicate bacteria which are only susceptible to high concentration of the drug, while maintaining a sustained release of anti-infective over time for the bacteria which are more susceptible to the long exposure rather than brief high peaks. The liposomal encapsulation can also aid the penetration of the biofilms and the protracted exposure is likely more effective against dormant or slowly replicating bacteria. While some aspects of biofilm resistance are poorly understood, the dominant mechanisms are thought to be related to: (i) modified nutrient environments and suppression of growth rate within the biofilm; (ii) direct interactions between the exopolymer matrices, and their constituents, and antimicrobials, affecting diffusion and availability; and (iii) the development of biofilm/attachment-specific phenotypes (Gilbert P et al., 1997). The intent of the immediate-release anti-infective; e.g., ciprofloxacin, is thus to rapidly increase the antibiotic concentration in the lung to therapeutic levels around the difficult to eradicate bacteria. These high peaks in combination with the better penetration of liposomes into biofilms also address the challenges of lower diffusion rate of the unencapsulated antibiotic to and within the biofilm. The sustained-release anti-infective; e.g., ciprofloxacin, serves to maintain a therapeutic level of antibiotic in the lung thereby providing continued therapy over a longer time frame, increasing efficacy, reducing the frequency of administration, and reducing the potential for resistant colonies to form.

The sustained release of the anti-infective may ensure that the anti-infective agent never falls below the sub-inhibitory concentration and so reduces the likelihood of forming resistance to the anti-infective.

Another aspect of the invention is related to methods of treatment of intracellular infections, and in particular in the lung. Some liposome formulations are known to be taken up by macrophages, for example alveolar macrophages, which are the site of intracellular infections. Thus delivery using certain liposome formulations will increase the ability to target the encapsulated drug to the macrophages which contain the intracellular infections. However, significant amounts of encapsulated drug may be released from the liposomes during the nebulization process or after deposition in the airways, prior to uptake by the macrophages. By creating a liposome formulation which is stable to nebulization, and furthermore, which is retained within the liposomes for longer periods of time, it is possible to enhance the ability to target encapsulated drug to the macrophages, or other cells with the intracellular infections. Liposomes which contain drug in nanocrystals consisting of a relatively poorly soluble drug form will have a slower rate of release from the liposomes, due to the requirement for the crystalline drug to dissolve prior to transport across the liposome bilayer. Thus, it is expected that this may also lead to a reduction in the in vivo release rate, thereby further increasing the ability to target intracellular infections in the lung using the formulations of this invention.

Although ciprofloxacin is a particularly useful anti-infective in this invention, there is no desire to limit this invention to ciprofloxacin. Other antibiotics or anti-infectives can be used such as those selected from the group consisting of: an aminoglycoside, a tetracycline, a sulfonamide, p-aminobenzoic acid, a diaminopyrimidine, a quinolone, a .beta.-lactam, a .beta.-lactam and a .beta.-lactamase inhibitor, chloraphenicol, a macrolide, penicillins, cephalosporins, corticosteroid, prostaglandin, linomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, a polyene antifungal, flucytosine, imidazole, triazole, griseofulvin, terconazole, butoconazole ciclopirax, ciclopirox olamine, haloprogin, tolnaftate, naftifine, terbinafine, peptide antibiotics or any combination thereof.

An aspect of the invention is a formulation, comprising:
liposomes wherein the liposomes comprise:
a lipid bilayer; and
a cryopreservative;
nanocrystals of a pharmaceutically active drug surrounded by the lipid bilayer wherein the nanocrystals have dimensions of 200 nm or less.

Another aspect of the invention is the formulation comprising a surfactant such as a non-ionic detergen in combination with a cryopreservative which is a polyol such as trehalose and sucrose.

Another aspect of the invention the formulation includes a pharmaceutically acceptable carrier and the carrier may alternatively be a pharmaceutically active drug in liquid form or an aqueous carrier with drug dissolved therein.

In another aspect of the invention the pharmaceutically active drug is an anti-infective drug which may be selected from the group consisting of a quinolone, a sulfonamide, an aminoglycoside, a tetracycline, para-aminobenzoic acid, a diaminopyrimidine, a beta-lactam, a beta-lactam and a beta-lactamase inhibitor, chloramphenicol, a macrolide, lincomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, polyene antifungal, flucytosine, imidazole, triazole, griseofulvin, terconazole, butoconazole ciclopirax, ciclopirox olamine, haloprogin, tolnaftate, naftifine, terbinafine and combinations thereof.

Another aspect of the invention is the formulation wherein the bilayer is comprised of a lipid selected from the group consisting of: fatty acids; lysolipids; sphingolipids; sphingomyelin; glycolipids; glucolipids; glycosphingolipids; palmitic acid; stearic acid; arachidonic acid; oleic acid; lipids bearing sulfonated mono-, di-, oligo- or polysaccharides; lipids with ether and ester-linked fatty acids, polymerized lipids, diacetyl phosphate, stearylamine, cardiolipin, phospholipids, synthetic phospholipids with asymmetric acyl chains; and lipids bearing a covalently bound polymer.

Another aspect of the invention is the formulation wherein the liposome comprises a phospholipid selected from the group consisting of phosphatidylcholines, lyso-phosphatidylcholines, phosphatidylethanolamines, phosphatidylinositols, phosphatidylglycerols, phosphatidic acid, phosphatidylserines, and mixtures thereof; wherein said phospholipid is provided in admixtures with a modifying agent selected from the group consisting of cholesterols, stearyl amines, stearic acid, tocopherols, and mixtures thereof; and wherein the liposomes are unilamellar or multilamellar.

Another aspect of the invention includes formulations wherein the nanocrystals have dimensions of 10 nanometers or less, the cryopreservative is a sucrose or trehalose, the surfactant is a polysorbate surfactant such as polysorbate 20 and BRIJ 30 and wherein the drug is preferably ciprofloxacin.

In another aspect of the invention the formulation is aerosolized and the aerosolized particles have an aerodynamic diameter in a rage of from 1 micron to 12 microns and when aerosolized 90% or more, 95% or more, 98% or more of the liposomes maintain their structural integrity.

In another aspect of the invention the formulation is frozen by reducing the temperature to a range of from −20° C. to −80° C., stored for one week or more followed by thawing at a temperature in a range of 5° C. to 30° C. after which 90% or more of the liposomes maintain their structural integrity or 95% or more, or 98% or more of the liposomes maintain their structural integrity.

Another aspect of the invention is using any of the formulations as described here with a drug therein and using that formulation in order to adjust a drug release profile of the formulation by adjusting the amount of surfactant to obtain a desired release rate.

Another aspect of the invention is a method of treating an infection in a patient, comprising:

aerosolizing a formulation comprising a free first pharmaceutically active drug and a second pharmaceutically active drug encapsulated in liposomes in the form of nanocrystals formed after freeze thaw; and inhaling the aerosol into the patient's lungs wherein the free drug comprises between 1% and 50% of the total of both free drug and encapsulated drug in the formulation.

Another aspect is the method as described above wherein the infection is an infection of a microorganism selected from the group consisting of mycobacteria, *P. aeruginosa* and *F. tularensis.*

Another aspect of the invention is a method wherein:

90% or more of the liposomes maintain integrity when aerosolized and after contacting lung tissue provide a ciprofloxacin release rate of 0.5% to 10% per hour.

Another aspect of the invention is a method wherein:

95% or more of the liposomes maintain integrity when aerosolized and after contacting lung tissue provide a ciprofloxacin release rate of 1% to 8% per hour.

Another aspect of the invention is a method wherein:

the liposomes comprise cholesterol and hydrogenated soy phosphatidyl-choline (HSPC) at a ratio of 29.4 to 70.6, and are unilamellar and wherein 98% or more of the liposomes maintain integrity when aerosolized, and provide a ciprofloxacin release rate of 2% to 6% per hour.

Another aspect of the invention is a method wherein:

the liposomes are further comprised of 0.1 to 0.3% polysorbate 20, and 200 to 400 mg/mL sucrose.

An aspect of the invention is a method of adjusting a drug release profile, comprising:

adding a surfactant to the formulation as claimed in any of claims 1 and 21 and adjusting the amount of surfactant to obtain a desired drug release rate;

wherein the surfactant is a nonionic detergent; and wherein the surfactant is selected from the group consisting of polysorbate 20 and BRIJ 30.

Another aspect of the invention is a method of treatment whereby any method as described above is carried out based on a measured symptom of a patient; and administering of the formulation is carried out by a route selected from the group consisting of injection, inhalation, nasal administration, orally, and IV infusion.

An aspect of the invention is a method of treating an infection in a patient, comprising:

aerosolizing a formulation comprising a free first pharmaceutically active drug and a second pharmaceutically active drug encapsulated in liposomes in the form of nanocrystals formed after freeze thaw; and inhaling the aerosol into the patient's lungs wherein the free drug comprises between 1% and 50% of the total of both free drug and encapsulated drug in the formulation;

wherein the infection is an infection of a microorganism selected from the group consisting of mycobacteria, P. aeruginosa and F. tularensis.

An aspect of the invention is a method of treating an antibiotic resistant infection in a patient, comprising:

aerosolizing a formulation comprising 30% free ciprofloxacin and 70% ciprofloxacin encapsulated in liposomes; and inhaling the aerosol into the patient's lungs whereby 90% or more of the liposomes maintain structural integrity after being aerosolized, wherein the antibiotic resistant infection comprises microorganisms in a biofilm or microorganisms engulfed in macrophage;

wherein the infection is an infection of microorganisms in a biofilm;

wherein the infection is an infection of microorganisms engulfed in macrophage;

wherein the infection is an infection of microorganisms selected from the group consisting of mycobacteria, P. aeruginosa and F. tularensis;

wherein the liposomes have an average particle size of about 75 nm to about 120 nm and are unilamellar;

wherein the liposomes are comprised of cholesterol and hydrogenated soy phosphatidyl-choline (HSPC)—a semi-synthetic fully hydrogenated derivative of nature soy lecithin at a ratio of about 30 to 70 (plus or minus 10%);

wherein the formulation further comprising an excipient suitable for pulmonary delivery comprised of sodium acetate and an isotonic buffer;

wherein 90% or more of the liposomes maintain integrity when aerosolized and after contacting lung tissue provide a ciprofloxacin release rate of 0.5% to 10% per hour;

wherein 95% or more of the liposomes maintain integrity when aerosolized and after contacting lung tissue provide a ciprofloxacin release rate of 1% to 8% per hour.

The invention further includes any method as described here, wherein the liposomes comprise cholesterol and hydrogenated soy phosphatidyl-choline (HSPC) at a ratio of 29.4 to 70.6, and are unilamellar and wherein 98% or more of the liposomes maintain integrity when aerosolized, and provide a ciprofloxacin release rate of 2% to 6% per hour.

The invention further includes any method as described here, wherein the liposomes are further comprised of 0.1 to 0.3% polysorbate 20, and 200 to 400 mg/mL sucrose.

The invention further includes any method as described here, wherein the aerosolizing and inhaling are repeated once each day over a period of seven days or more.

The invention further includes any method as described here, wherein the aerosolizing and inhaling are repeated once each day over a period of seven days to fifty-six days.

The invention further includes any method as described here, wherein the formulation comprises 50 mg to 500 mg of ciprofloxacin.

The invention further includes any method as described here, wherein the formulation comprises 75 mg to 300 mg of ciprofloxacin.

The invention further includes any method as described here, wherein the formulation is nebulized and comprises 150 mg of ciprofloxacin.

These and other objects, advantages, and features of the invention will become apparent to those persons skilled in the art upon reading the details of the formulations and methodology as more fully described below.

BRIEF DESCRIPTION OF THE DRAWINGS

Aspects and embodiments of the invention are best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1 is a graph showing the encapsulation of ciprofloxacin following freeze-thaw at −50° C., as a function of the ratio of surfactant (polysorbate 20) to lipid in the liposomes. Nine formulations are studied with varying ratios of sucrose to lipid (2:1, 3:1 and 4:1) and three concentrations of ciprofloxacin 10, 12.5 and 15 mg/mL). There appears to be a range in the percent drug encapsulation that can be achieved following freeze-thaw. Thus the desired % encapsulation can be designed into the formulation depending upon the choice of surfactant, surfactant concentration, ratio of surfactant to lipid in the liposomes, drug concentration, choice of sugar, sugar concentration, and ratio of sugar to lipid in the liposomes.

FIG. 2 is a similar graph to FIG. 1 except that it is after each formulation remained frozen for 6 weeks prior to thawing. Nine formulations are studied with varying ratios of sucrose to lipid (2:1, 3:1 and 4:1) and three concentrations of ciprofloxacin 10, 12.5 and 15 mg/mL). There appears to be a range in the percent drug encapsulation that can be achieved following freeze-thaw. Thus the desired % encapsulation can be designed into the formulation depending upon the choice of surfactant, surfactant concentration, ratio of surfactant to lipid in the liposomes, drug concentration, choice of sugar, sugar concentration, and ratio of sugar to lipid in the liposomes.

FIG. 3 is a cryoTEM micrograph showing the presence of ciprofloxacin nanocrystals in the liposomes after freeze-thaw. The scale bar is 100 nm. The formulation was 12.5 mg/mL liposomal ciprofloxacin that contained 67.5 mg/mL sucrose and 0.1% polysorbate 20. The lipid content was approximately 22.5 mg/mL implying a ratio of sucrose to lipid of approximately 3:1 on a weight basis. The cryoTEM was performed by diluting the sample from 12.5 mg/mL ciprofloxacin to 5 mg/mL and then freezing the samples in liquid ethane and vitrification.

FIG. 4 is a cryoTEM micrograph of the same liposome formulation prior to freeze thaw, demonstrating the absence of nanocrystals or precipitated drug in the liposomes. The methodology was as described in FIG. 3.

FIG. 5 through FIG. 9 show profiles of the In Vitro Release (IVR) rate of encapsulated ciprofloxacin from specific liposome formulations. The IVR methodology is described in Cipolla et al (2014).

FIG. 10 through 12 show cryoTEM images of CFI formulations after freeze-thaw.

FIG. 13 shows cryoTEM image of the CFI formulation in FIG. 11 after freeze-thaw and subsequent mesh nebulization using the PARI eFlow nebulizer.

DETAILED DESCRIPTION OF THE INVENTION

Before the present method of formulating ciprofloxacin-encapsulated liposomes and delivery of such for prevention and/or treatment of cystic fibrosis and other medical conditions, and devices and formulations used in connection with such are described, it is to be understood that this invention is not limited to the particular methodology, devices and formulations described, as such methods, devices and formulations may, of course, vary. It is also to be understood that the terminology used herein is for the purpose of describing particular embodiments only, and is not intended to limit the scope of the present invention which will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a formulation" includes a plurality of such formulations and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As used herein, anti-infective refers to agents that act against infections, such as bacterial, viral, fungal, mycobacterial, or protozoal infections.

Anti-infectives covered by the invention include but are not limited to quinolones (such as nalidixic acid, cinoxacin, ciprofloxacin and norfloxacin and the like), sulfonamides (e.g., sulfanilamide, sulfadiazine, sulfamethaoxazole, sulfisoxazole, sulfacetamide, and the like), aminoglycosides (e.g., streptomycin, gentamicin, tobramycin, amikacin, netilmicin, kanamycin, and the like), tetracyclines (such as chlortetracycline, oxytetracycline, methacycline, doxycycline, minocycline and the like), para-aminobenzoic acid, diaminopyrimidines (such as trimethoprim, often used in conjunction with sulfamethoxazole, pyrazinamide, and the like), penicillins (such as penicillin G, penicillin V, ampicillin, amoxicillin, bacampicillin, carbenicillin, carbenicillin indanyl, ticarcillin, azlocillin, mezlocillin, piperacillin, and the like), penicillinase resistant penicillin (such as methicillin, oxacillin, cloxacillin, dicloxacillin, nafcillin and the like), first generation cephalosporins (such as cefadroxil, cephalexin, cephradine, cephalothin, cephapirin, cefazolin, and the like), second generation cephalosporins (such as cefaclor, cefamandole, cefonicid, cefoxitin, cefotetan, cefuroxime, cefuroxime axetil, cefinetazole, cefprozil, loracarbef, ceforanide, and the like), third generation cephalosporins (such as cefepime, cefoperazone, cefotaxime, ceftizoxime, ceftriaxone, ceftazidime, cefixime, cefpodoxime, ceftibuten, and the like), other beta-lactams (such as imipenem, meropenem, aztreonam, clavulanic acid, sulbactam, tazobactam, and the like), beta-lactamase inhibitors (such as clavulanic acid), chloramphenicol, macrolides (such as erythromycin, azithromycin, clarithromycin, and the like), lincomycin, clindamycin, spectinomycin, polymyxin B, polymixins (such as polymyxin A, B, C, D, E.sub.1 (colistin A), or E.sub.2, colistin B or C, and the like) colistin, vancomycin, bacitracin, isoniazid, rifampin, ethambutol, ethionamide, aminosalicylic acid, cycloserine, capreomycin, sulfones (such as dapsone, sulfoxone sodium, and the like), clofazimine, thalidomide, or any other antibacterial agent that can be lipid encapsulated. Anti-infectives can include antifungal agents, including polyene antifungals (such as amphotericin B, nystatin, natamycin, and the like), flucytosine, imidazoles (such as miconazole, clotrimazole, econazole, ketoconazole, and the like), triazoles (such as itraconazole, fluconazole, and the like), griseofulvin, terconazole, butoconazole ciclopirax, ciclopirox olamine, haloprogin, tolnaftate, naftifine, terbinafine, or any other antifungal that can be lipid encapsulated or complexed and pharmaceutically acceptable salts thereof and combinations thereof. Discussion and the examples are directed primarily toward ciprofloxacin but the scope of the application is not intended to be limited to this anti-infective. Combinations of drugs can be used.

A biofilm is any group of microorganisms in which cells stick to each other on a surface. These adherent cells are frequently embedded within a self-produced matrix of extracellular polymeric substance (EPS). Biofilm extracellular polymeric substance, which is also referred to as slime (although not everything described as slime is a biofilm), is a polymeric conglomeration generally composed of extracellular DNA, proteins, and polysaccharides. Biofilms may form on living or non-living surfaces and can be prevalent in natural, industrial and hospital settings. The microbial cells growing in a biofilm are physiologically distinct from planktonic cells of the same organism, which, by contrast, are single-cells that may float or swim in a liquid medium.

Biofilms have been found to be involved in a wide variety of microbial infections in the body, by one estimate 80% of all infections. Infectious processes in which biofilms have been implicated include common problems such as urinary tract infections, catheter infections, middle-ear infections, formation of dental plaque, gingivitis, coating contact lenses, and less common but more lethal processes such as endocarditis, infections in cystic fibrosis, and infections of permanent indwelling devices such as joint prostheses and heart valves. More recently it has been noted that bacterial biofilms may impair cutaneous wound healing and reduce topical antibacterial efficiency in healing or treating infected skin wounds.

Bronchodilators covered by the invention include but are not limited to $\beta_2$-adrenergic receptor agonists (such as albuterol, bambuterol, salbutamol, salmeterol, formoterol, arformoterol, levosalbutamol, procaterol, indacaterol, carmoterol, milveterol, procaterol, terbutaline, and the like), and antimuscarinics (such as trospium, ipratropium, glycopyrronium, aclidinium, and the like). Combinations of drugs may be used.

Anti-inflammatories covered by the invention include but are not limited to inhaled corticosteroids (such as beclometasone, budesonide, ciclesonide, fluticasone, etiprednol, mometasone, and the like), leukotriene receptor antagonists and leukotriene synthesis inhibitors (such as montelukast, zileuton, ibudilast, zafirlukast, pranlukast, amelubant, tipelukast, and the like), cyclooxygenase inhibitors (such as ibuprofen, ketoprofen, ketorolac, indometacin, naproxen, zaltoprofen, lornoxicam, meloxicam, celecoxib, lumiracoxib, etoricoxib, piroxicam, ampiroxicam, cinnoxicam, diclofenac, felbinac, lornoxicam, mesalazine, triflusal, tinoridine, iguratimod, pamicogrel, and the like). Combinations of drugs may be used.

As used herein, "Formulation" refers to the liposome-encapsulated anti-infective, with any excipients or additional active ingredients, either as a dry powder or suspended or dissolved in a liquid.

The terms "subject," "individual," "patient," and "host" are used interchangeably herein and refer to any vertebrate, particularly any mammal and most particularly including human subjects, farm animals, and mammalian pets. The subject may be, but is not necessarily under the care of a health care professional such as a doctor.

A "stable" formulation is one in which the protein or enzyme therein essentially retains its physical and chemical stability and integrity upon storage and exposure to relatively high temperatures. Various analytical techniques for measuring peptide stability are available in the art and are reviewed in Peptide and Protein Drug Delivery, 247-301, Vincent Lee Ed., Marcel Dekker, Inc., New York, N.Y., Pubs. (1991), and Jones, A. (1993) *Adv. Drug Delivery Rev.* 10:29-90. Stability can be measured at a selected temperature for a selected time period.

"Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the claimed methods and compositions.

Polysorbate 20 is a surfactant and some common commercial brand names include Alkest TW 20 and Tween 20. Chemically it is a polysorbate surfactant whose stability and relative non-toxicity allows it to be used in pharmacological applications. It is a polyoxyethylene derivative of sorbitan monolaurate, and is distinguished from the other members in the polysorbate range by the length of the polyoxyethylene chain and the fatty acid ester moiety.

BRIJ 30 is a Surfactant. Chemically it is a polyoxyethylenated straight chain alcohol, having an average molecular weight of 362. It has an empirical formula of

$$C_{12}H_{25}(OCH_2CH_2)_4OH.$$

INVENTION IN GENERAL

Ciprofloxacin is a well-established and extensively utilized broad-spectrum fluoroquinolone antibiotic that is indicated for the treatment of lower respiratory tract infections due to *P. aeruginosa*, which is common in patients with cystic fibrosis. The primary advantage of inhaled antimicrobials is that they target antibiotic delivery to the area of primary infection and bypass GI-related side effects; however, the poor solubility and bitterness of the drug have limited development of a formulation suitable for inhalation. Furthermore, the rapid tissue distribution of ciprofloxacin means a short drug residence time in the lung thus limiting therapeutic benefit over oral or IV drug administration. A liposome-encapsulated formulation of ciprofloxacin that can be frozen, and after thawing provides a modified bi-phasic release profile, will decrease the limitations and improve management of pulmonary infections due to *P. aeruginosa* pulmonary infections in patients with CF through improved biopharmaceutical characteristics and mechanisms such as altered drug PK and biodistribution, sustained drug release from the carrier, enhanced delivery to disease sites, and protection of the active drug species from degradation.

The invention includes a formulation that combines ciprofloxacin (or a different immune blunting agent; e.g., zithromax) with another drug; e.g., liposomal ciprofloxacin, delivered via the inhalation route. The liposomal encapsulated ciprofloxacin may be substituted with an antibiotic other than ciprofloxacin and may be formulated without using liposomes. The other drug does not have to be an antibiotic and may be any drug that is believed to have some beneficial properties when delivered to the lung. One or more of these drugs also form liposomally encapsulated nanocrystals during the freeze-thaw process.

The invention is not limited to the treatment of patients with PA or NTM lung infections but includes other intracellular infections and general lung infections including patients with CF. In fact, there are many patients and indications for which this therapy may be beneficial, including non-CF bronchiectasis, pneumonia, and other lung infections. This treatment paradigm would also apply to other lung diseases including COPD, asthma, pulmonary hypertension and others in which a formulation of free and encapsulated ciprofloxacin is delivered in combination with another drug to allow higher dosing of the other drug or safer administration of the other drug.

The invention also relates to the use of inhaled free ciprofloxacin (or a different immune blunting agent; e.g., zithromax) in combination with other drugs given via inhalation. These other drugs may include nucleotides (DNA, RNA, siRNA), enzymes to reduce the viscoelasticity of the mucus such as DNase and other mucolytic agents, chemicals to upregulate the chloride ion channel or increase flow of ions across the cells, nicotine, P2Y2 agonists, elastase inhibitors including Alpha-1 antitrypsin (AAT), N-acetylcysteine, antibiotics and cationic peptides, such as lantibiotics, and specifically duramycin, short-acting bronchodilators (e.g., β2-adrenergic receptor agonists like albuterol or indacaterol), M3 muscarinic antagonists (e.g., ipatropium bromide), K+-channel openers, long-acting bronchodilators (e.g., formoterol, salmeterol), steroids (e.g., budesonide, fluticasone, triamcinolone, beclomethasone, ciclesonide, etc.), xanthines, leukotriene antagonists (e.g., montelukast sodium), phosphodiesterase 4 inhibitors, adenosine receptor antagonists, other miscellaneous anti-inflammatories (e.g., Syk kinase inhibitors (AVE-0950), tryptase inhibitors (AVE-8923 & AVE-5638), tachykinin antagonists (AVE-5883), inducible nitric oxide synthase inhibitors (GW-274150) and others), transcription factor decoys, TLR-9 agonists, antisense oligonucleotides, siRNA, DNA, CGRP, lidocaine, inverse β2-agonists, anti-infective oxidative therapies, cytokine modulators (e.g., CCR3 receptor antagonists (GSK-766994, DPC-168, AZD-3778), TNF-α production inhibitors (LMP-160 & YS-TH2), and IL-4 antagonists (AVE-0309)), small molecule inhibitors of IgE, cell adhesion molecule (CAM) inhibitors, small molecules targeting the VLA4 receptor or integrin α4β1 (e.g., R-411, PS-460644, DW-908e, & CDP-323), immunomodulators including those that block T-cell signaling by inhibition of calcineurin (Tacrolimus), heparin neutralizers (Talactoferrin alfa), cytosolic PLA2 inhibitors (Efipladib), or combinations thereof. The delivery of the combination products may be achieved by combining the drugs into one stable formulation, or providing the drugs in separate containers to be combined at the time of administration or alternatively by sequentially delivering the products.

The compositions of the invention can be prepared from liquid formulations of liposomes containing a polyol and a surfactant. Such ingredients can, e.g., provide protection to the bioactive material, structural stability, enhanced solubility, and other desirable characteristics to the compositions. Polyols of the compositions can be present in the liquid formulation in an amount ranging from about 1 weight percent to up to 40 weight percent, or from about 5 weight percent to about 20 weight percent. A "polyol" is a substance with multiple hydroxyl groups, and includes sugars (reducing and nonreducing sugars), sugar alcohols and sugar acids. Preferred polyols herein have a molecular weight which is less than about 600 kDa (e.g. in the range from about 120 to about 400 kDa). A "reducing sugar" is a polyol which contains a hemiacetal group that can reduce metal ions or react covalently with lysine and other amino groups in proteins. A "nonreducing sugar" is a sugar which does not have these properties of a reducing sugar. Examples of reducing sugars are fructose, mannose, maltose, lactose, arabinose, xylose, ribose, rhamnose, galactose and glucose. Nonreducing sugars include, e.g., sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof. The polyols can include, e.g., sucrose, trehalose, sorbose, melezitose, raffinose, mannitol, xylitol, erythritol, threitol, sorbitol, glycerol, fructose, mannose, maltose, lactose, arabinose, xylose, ribose, rhamnose, galactose, glucose, L-gluconate, and/or the like.

Surfactants of the compositions can be present in the liquid formulations in amounts ranging from about 0.01 weight percent to about 2 weight percent. The surfactants can include, e.g., nonionic detergents, such as polyethylene glycol sorbitan monolaurate (Tween 20, or polysorbate 20), polyoxyethylenesorbitan monooleate (Tween 80, or polysorbate 80), BRIJ 30, block copolymers of polyethylene and polypropylene glycol (Pluronic), and/or the like. Surfactants can also include alkylphenyl alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, silicone oils, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers, polyacrylates, acrylic acid graft copolymers, alkylarylsulfonates, phenylsulfonates, alkyl sulfates, alkyl sulfonates, alkyl ether sulfates, alkyl aryl ether sulfates, alkyl polyglycol ether phosphates, polyaryl phenyl ether phosphates, alkylsulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes, lignin-sulfite waste liquor, alkyl phosphates, quaternary ammonium compounds, amine oxides, betaines, and/or the like.

The compositions can include other ingredients, such as a pH buffer, other drugs, and other excipients. Buffers of the compositions can include, e.g., potassium phosphate, sodium phosphate, sodium acetate, sodium citrate, histidine, glycine, arginine, phosphate, imidazole, sodium succinate, ammonium bicarbonate, and/or a carbonate, to maintain pH at between about pH 3 to about pH 8, or about pH 4 to pH 6 or around pH 5.

The invention includes a method of treatment whereby the formulation of the invention is administered by any known route of administration such as injection, inhalation, nasal administration, orally, and IV infusion. Although a preferred method of administration is by inhalation in that the invention is particularly suited for the treatment of infections in the form of biofilms in the lungs. The formulations of the invention are particular suited for the eradication of infections formed as biofilms in the lung for a number of reasons. First, the liposomes of the invention are particular resistant to rupture upon aerosolization in that 90% or more, 95% or more, 98% or more of the liposomes maintain their structural integrity and thereby maintain the drug formulations held within them after being aerosolized either by a nebulizer or being moved through the pores of a porous membrane. After the formulation reaches lung tissue, drug dissolved in the solvent carrier, which may be an aqueous carrier at a relatively low pH such as 6.5 or less, 6.0 or less, 5.5 or less, 5.0 or less, drug in that carrier provides for immediate release and contact with bacteria. Thereafter, the liposomes dissolve or their bilayers become more permeable, and provide for release of formulation encapsulated within the liposomes. Thereafter, the nanocrystals slowly dissolve. Accordingly, the formulations of the invention can be delivered on a once a day basis and provided for controlled release of the drug such as ciprofloxacin over a long period of time.

Biofilms are resistant to eradication by antibiotics due to a number of factors. First, they are usually surrounded by a dense exopolysaccharide matrix that inhibits the diffusion of some antibiotics, including aminoglycosides as a class, into the biofilm. Second, the outer layer of faster-growing bacteria cells also "protects" the cells in the interior of the biofilm from antibiotic exposure. Third, the cells in the interior of the biofilm are oxygen-deprived and so are slower-growing or dormant and thus intrinsically less sensitive to antibiotic exposure. Finally, there is evidence of the presence of "persister" cells which are invulnerable to killing and other unknown resistance mechanisms may also exist.

I. Generation of Liposomes Containing Ciprofloxacin Nanocrystals

Most liposome formulations are not stable to freezing. As the vialed formulation is subjected to temperatures below freezing, the water in contact with the cold surface (e.g., usually the bottom or sides of the vial) will preferentially start to freeze forming water crystals, resulting in the excipients and other components in the formulation becoming more concentrated in the remaining liquid volume. Over time all of the liquid will eventually freeze but this concentrating effect is known to reduce the stability of many products. The pH can also change during the freezing process and in the frozen state and this can also affect the stability of the formulation. Finally, the freezing process itself can compromise the supramolecular phospholipid assembly. Liposomes are particularly unstable to the freezing process because water is present both in the interior and exterior of the lipid bilayer. The lipid bilayer can form hydrogen bonds with the water molecules. As the water crystals form, they can cause liposome vesicles to rupture. Upon thawing, the lipid components will not reform into vesicles but instead they will remain in a precipitated or agglomerated state.

Lyophilization or spray-drying can cause liposome fusion and phase separation during drying and rehydration. The addition of sugars; e.g., sucrose and trehalose, can stabilize some liposome preparations during freeze-drying or spray drying during which water is removed by sublimation or evaporation, respectively. Cryo/lyoprotectants limit mechanical damage and rupture of the lipid bilayer caused by ice crystals during the freeze-drying and the rehydration process by maintaining the membrane in a flexible state, by adding bulk to the solution to prevent direct contact between vesicles and reduce mobility of vesicles. The sugar molecules can form hydrogen bonds with the liposome and thus "replace" the water molecules around the liposome. Initial experiments showed the addition of sugars did not stabilize the liposome formulation with respect to freeze-drying or spray-drying. However, further experiments show that various combinations of a sugar with surfactant, in this case, polysorbate 20, did stabilize the liposome to freezing. Upon thawing, the preparation remained clear with a small change in the mean vesicle size of only a few nm for specific added concentrations of polysorbate 20. The unilamellar vesicles, upon freeze-thaw, did not form multi-lamellar vesicles when formulated with sugar and surfactant in a specific fashion. This is in contrast to the large 300-700 nm multilamellar vesicles which formed after freeze-thaw in some cases when only the sugar was added to the liposomal ciprofloxacin for inhalation (CFI) formulation: many of the vesicles were so destabilized that they formed agglomerates and precipitated out of solution.

Surprisingly, we found that the addition of a combination of sucrose and polysorbate 20 to the CFI drug product resulted in a formulation that could be frozen and maintained its supramolecular liposome structure upon thawing, with limited change in the vesicle size distribution and retention of the majority of the encapsulated drug. The addition of surfactant alone, without sucrose or another sugar, did not allow the liposomes to retain their structure after freeze-thaw. Other cryoprotectants, including sugars such as trehalose, could also work in combination with Tween 20. This has been demonstrated for trehalose. This invention is not limited to Tween 20 as the sole surfactant with such ability but rather the use of Tween 20 for the purpose shown here is provided as an example of the invention.

Another novel aspect of this invention is that the specific concentration of sugar and surfactant in the formulation will determine how much free drug is released from the liposomes after freeze-thaw (FIG. 1). Judicious choice of those excipient concentrations will allow a wide range of encapsulated and free drug to be created in the final vial. One embodiment is to create a stable frozen formulation that after thawing matches the composition and specific property of an existing formulation, such as the mixture of approximately 30% free ciprofloxacin and 70% liposomally encapsulated ciprofloxacin (Pulmaquin®). This could be achieved by addition of ~0.1 to 0.3% Tween 20 and 200 to 400 mg/mL sucrose.

One long term stability study demonstrated that keeping the vials frozen for 6 weeks before thawing resulted in similar proportions of free and encapsulated drug as for an immediate freeze-thaw (FIG. 2). Thus another aspect of this invention is the potential to store a liposomal drug product for many years and reduce lipid degradation and physical instability.

Surprisingly, we have also found that it may be possible to create drug nanocrystals inside the liposomes for specific combinations of sucrose and surfactant. If the sugar concentrations are adequately high to prevent liposome destruction and/or agglomeration after freeze-thaw, one can form nanocrystals of ciprofloxacin inside the vesicles which cause the vesicles to lose their circular shape and form ellipsoid shapes. The nanocrystals may be on the order of 100 nm in length and form inside the liposome vesicles (FIG. 3). Some of the liposomes may have lost some or their entire encapsulated drug content, the amount of free drug is dependent upon the amount of added surfactant. FIG. 3 shows the presence of liposomes which do not contain nanocrystals, and which are lighter in density, consistent with having lost some, or all, of their encapsulated drug. A cryoTEM micrograph of the same formulation prior to freeze-thaw indicates the absence of nanocrystals (FIG. 4) and the liposomes are of darker shading, indicating the presence of drug within. These images confirm that the nanocrystals are formed in response to freeze-thaw.

According to aspects of the instant invention, a method is provided for formulating ciprofloxacin and other anti-infectives by encapsulating these drugs in liposomes. Composed of naturally-occurring materials which are biocompatible and biodegradable, liposomes are used to encapsulate biologically active materials for a variety of purposes. Having a variety of layers, sizes, surface charges and compositions, numerous procedures for liposomal preparation and for drug encapsulation within them have been developed, some of which have been scaled up to industrial levels. Liposomes can be designed to act as sustained release drug depots and, in certain applications, aid drug access across cell membranes.

The sustained release property of the liposomes may be regulated by the nature of the lipid membrane and by the inclusion of other excipients in the composition of the liposomes. The rate of drug release has been primarily controlled by changing the nature of the phospholipids, e.g. hydrogenated (--H) or unhydrogenated (--G), or the phospholipid/cholesterol ratio (the higher this ratio, the faster the rate of release), the hydrophilic/lipophilic properties of the active ingredients and by the method of liposome manufacturing. A key aspect of our invention that the rate of drug release can be also controlled by formation of nanocrystals within the liposomes, and more specifically by their formation through a freeze-thaw process using specific formulation tools and excipients.

II. Pharmaceutical Formulation of Ciprofloxacin-Containing Liposomes

In a preferred embodiment, the liposome-encapsulated ciprofloxacin is administered to a patient in an aerosol inhalation device but could be administered by the IV route, by injection or another route of delivery. In some embodiments, ciprofloxacin is encapsulated in the liposomes in combination with other pharmaceuticals that are also encapsulated. In some embodiments, ciprofloxacin is encapsulated in the liposomes in combination with other pharmaceuticals that are not encapsulated. In some embodiments, the liposomes are administered in combination with ciprofloxacin that is not encapsulated, with pharmaceuticals that are not encapsulated, or various combinations thereof.

Regardless of the form of the drug formulation, it is preferable to create droplets or particles for inhalation in the range of about 0.5 µm to 12 µm, preferably 1 µm to 6 µm, and more preferably about 2-4 µm. By creating inhaled particles which have a relatively narrow range of size, it is possible to further increase the efficiency of the drug delivery system and improve the repeatability of the dosing. Thus, it is preferable that the particles not only have a size in the range of 0.5 µm to 12 µm or 2 µm to 6 µm or about 3-4 µm but that the mean particle size be within a narrow range so that 80% or more of the particles being delivered to a patient have a particle diameter which is within ±20% of the average particle size, preferably ±10% and more preferably ±5% of the average particle size.

The formulations of the invention may be administered to a patient using a disposable package and portable, handheld, battery-powered device, such as the AERx device (U.S. Pat. No. 5,823,178, Aradigm, Hayward, Calif.). Alternatively, the formulations of the instant invention may be carried out using a mechanical (non-electronic) device. Other inhalation devices may be used to deliver the formulations including conventional jet nebulizers, ultrasonic nebulizers, soft mist inhalers, dry powder inhalers (DPIs), metered dose inhalers (MDIs), and other systems. Preferably, the proportion of free ciprofloxacin to encapsulated ciprofloxacin should remain constant after nebulization compared to the initial proportion; i.e., there should be no damage to the liposomes during nebulization that would result in premature release of a portion of the encapsulated antibiotic. This finding observed with our novel formulations is unexpected (Niven R W and Schreier H, 1990) but ensures that the animal or human inhaling the aerosol will get a reproducible proportion of free to encapsulated drug depositing throughout the lung.

An aerosol may be created by forcing drug through pores of a membrane wherein the pores have a size in the range of about 0.25 to 6 microns (U.S. Pat. No. 5,823,178). When the pores have this size the particles which escape through the pores to create the aerosol will have a diameter in the range of 0.5 to 12 microns. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency, pressure, and other parameters based on the density and viscosity of the formulation keeping in mind that an object of some embodiments is to provide aerosolized particles having a diameter in the range of about 0.5 to 12 microns.

The liposome formulation may be a low viscosity liquid formulation. The viscosity of the drug by itself or in combination with a carrier should be sufficiently low so that the formulation can be forced out of openings to form an aerosol, e.g., using 20 to 200 psi to form an aerosol preferably having a particle size in the range of about 0.5 to 12 microns.

In an embodiment, a low boiling point, highly volatile propellant is combined with the liposomes of the invention and a pharmaceutically acceptable excipient. The liposomes may be provided as a suspension or dry powder in the propellant, or, in another embodiment, the liposomes are dissolved in solution within the propellant. Both of these formulations may be readily included within a container which has a valve as its only opening. Since the propellant is highly volatile, i.e. has a low boiling point, the contents of the container will be under pressure.

In accordance with another formulation, the ciprofloxacin-containing liposomes are provided in a solution formulation prior to freeze-thaw. Any formulation, which after freeze-thaw makes it possible to produce aerosolized forms of ciprofloxacin-containing liposomes with modified release rates which can be inhaled and delivered to a patient via the intrapulmonary route may be used in connection with the present invention.

III. Dosing Regimens

Based on the above, it will be understood by those skilled in the art that a plurality of different treatments and means of administration can be used to treat a single patient. Thus, patients already receiving such medications, for example, as intravenous ciprofloxacin or antibiotics, etc., may benefit from inhalation of the formulations of the present invention. Some patients may receive only ciprofloxacin-containing liposome formulations by inhalation. Such patients may have symptoms of cystic fibrosis, be diagnosed as having lung infections, including intracellular infections, or have symptoms of a medical condition, which symptoms may benefit from administration to the patient of an antibiotic such as ciprofloxacin. The formulations of the invention may also be used diagnostically. In an embodiment, for example, a patient may receive a dose of a formulation of the invention as part of a procedure to diagnose lung infections, wherein one of more of the patient's symptoms improves in response to the formulation.

A patient will typically receive a dose of about 0.01 to 10 mg/kg/day of ciprofloxacin ±20% or ±10%. This dose will typically be administered by at least one, preferably several "puffs" from the aerosol device. The total dose per day is preferably administered at least once per day, but may be divided into two or more doses per day. Some patients may benefit from a period of "loading" the patient with ciprofloxacin with a higher dose or more frequent administration over a period of days or weeks, followed by a reduced or maintenance dose. As cystic fibrosis is typically a chronic condition, patients are expected to receive such therapy over a prolonged period of time.

It has previously been shown that inhalation of liposome-encapsulated fluoroquinolone antibiotics may be effective in treatment of lung infections and were shown to be superior to the free or unencapsulated fluoroquinolone in a mouse model of *F. tularensis* (CA 2,215,716, CA 2,174,803 and CA 2,101,241). However, the authors did not anticipate the potential benefit of freezing the liposome formulation and after freeze-thaw providing a modified release profile, especially one in which there are nanocrystals within the liposomes which attenuate, or modify, the release of encapsulated drug. According to one aspect of the present invention, high concentrations of an antibiotic are delivered immediately while also providing a sustained release of the therapeutic over hours or a day.

Thus, as discussed above, the formulations according to some aspects of the invention include free or non-encapsulated ciprofloxacin in combination with the liposome-encapsulated ciprofloxacin. Such formulations may provide an immediate benefit with the free ciprofloxacin resulting in a rapid increase in the antibiotic concentration in the lung fluid surrounding the bacterial colonies or biofilm and reducing their viability, followed by a sustained benefit from the encapsulated ciprofloxacin which continues to kill the bacteria or decrease its ability to reproduce, or reducing the possibility of antibiotic resistant colonies arising. The skilled practitioner will understand that the relative advantages of the formulations of the invention in treating medical conditions on a patient-by-patient basis.

IV. Combination Therapies

Liposome formulations of the invention may be administered concurrently with other drugs as described here. For example, the liposomes of the invention may be used along with drugs such as DNase, a mucolytic agent, chemicals that upregulate the chloride ion channel or increase flow of ions across the epithelial surface of cells, a bronchodilator, a steroid, a P2Y2 agonist, an elastase inhibitor such as Alpha-1 antitrypsin (AAT), N-acetylcysteine, agents that enhance the activity of the antibiotic against biofilm bacteria such as sodium salicylate, interferon gamma, interferon alpha, or a fluoroquinolone selected from the group consisting of amifloxacin, cinoxacin, ciprofloxacin, danofloxacin, difloxacin, enoxacin, enrofloxacin, fleroxacin, irloxacin, lomefloxacin, miloxacin, norfloxacin, ofloxacin, pefloxacin, rosoxacin, rufloxacin, sarafloxacin, sparfloxacin, temafloxacin and tosufloxacin or an antibiotic selected from the group of tobramycin, colistin, azithromycin, amikacin, cefaclor (Ceclor), aztreonam, amoxicillin, ceftazidime, cephalexin (Keflex), gentamicin, vancomycin, imipenem, doripenem, piperacillin, minocycline, or erythromycin.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

V. Method of Treatment

Until now we have discussed primarily the application of this invention to treat infections in cystic fibrosis and non-CF bronchiectasis patients, and those with NTM infections. However, it will be obvious to one skilled in the art that this invention will have utility and advantages beyond those modalities. This method of treatment applies to other disease states which involve infections of the nasal passages, airways, inner ear, or lungs; including but not limited to: bronchiectasis, tuberculosis, pneumonia; including but not limited to ventilator associated pneumonia, community acquired pneumonia, bronchial pneumonia, lobar pneumonia; infections by *Streptococcus pneumoniae*, *Chlamydia*, *Mycoplasma* pneumonia, staphylococci, prophylactive treatment or prevention for conditions in which infection might arise, e.g., intubated or ventilated patients, infections in lung transplant patient, bronchitis, pertussis (whooping cough), inner ear infections, streptococal throat infections, inhalation anthrax, tularemia, or sinusitis.

EXPERIMENTAL

The following examples are put forth so as to provide those of ordinary skill in the art with a complete disclosure and description of how to make and use the present invention, and are not intended to limit the scope of what the inventors regard as their invention nor is it intended to represent that the experiment below is the only experiment performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Ciprofloxacin (50 mg/mL) is encapsulated into liposomes consisting of hydrogenated soy phosphatidyl-choline (HSPC) (70.6 mg/mL), a semi-synthetic fully hydrogenated derivative of natural soy lecithin (SPC), and cholesterol (29.4 mg/mL). The lipid is organized in a bilayer, with an average particle size of 75 to 120 nm. The sterile suspension is suspended in an isotonic buffer (25 mM histidine, 145 mM NaCl at pH 6.0, 300 mOsm/kg). These liposomal ciprofloxacin preparations contain approximately 1% unencapsulated ciprofloxacin and can be administered as an aerosol, for example by nebulization, to a patient. The liposomal ciprofloxacin can also be combined with free ciprofloxacin, at 20 mg/mL, in a sodium acetate buffer, and administered as an aerosol, to a patient.

Example 2

Preparations of liposomal ciprofloxacin (CFI) were made using batches ARA048, ARA51, and ARA52 at 50 mg/mL.

A CFI formulation at 12.5 mg/mL was prepared by diluting 0.25 mL of the 50 mg/mL CFI, with 0.5 mL of 180 mg/mL sucrose, with 0.1 mL of 1% polysorbate 20, 0.1 mL of pH 4 acetate buffer, and 0.05 mL water for a final concentration of 12.5 mg/mL CFI in 0.1% polysorbate 20, 90 mg/mL sucrose at ~pH 5.

One vial of each of these preparations were frozen (in liquid nitrogen) and then thawed to form the nanocrystals inside the liposomes. The percent encapsulation in the CFI samples was determined by measuring the free and total drug. The free drug ranged from ~1 to ~2 mg/mL which represented between 10 to 18% free drug. The percent encapsulation thus ranged from 82 to 90%.

TABLE 1

Free Drug and Percent Encapsulation:

| Sample | Free Drug (mg/mL) | % Free | % Encapsulated |
| --- | --- | --- | --- |
| LOT ARA51 | 1.02 | 9.7 | 90.3 |
| LOT ARA48 | 1.84 | 16.6 | 83.4 |
| LOT ARA52 | 2.04 | 18.0 | 82.0 |

The in vitro release profiles for these samples were compared to that of the control CFI sample which was not frozen and thus did not contain the nanocrystals. All CFI samples were diluted (12 µL @12.5 mg/mL) into 3.0 mL Hepes Buffered Saline (HBS) to reach a final concentration of 0.05 mg/mL CFI. Hyclone Serum, lot #AWC99946, catalog # SH30075.03, (mixture of containers) expiration March 2016 (3.0 mL) was added to the diluted CFI and after mixing, the tube was stored in ice water to prevent initiation of release (0.025 mg/mL CFI). From the vial, 0.5 mL aliquots were transferred to 10 individual HPLC vials for each formulation. Duplicate vials represented each time point. Excluding the two T=0 vials for each formulation, the 8x5=40 remaining vials were placed in the 37° C. shaking water bath. A stopwatch was started. After 30, 60, 120 and 240 minutes, duplicate vials were removed for each formulation and plunged into the ice water bath to terminate the reaction. To each vial containing the 0.5 mL sample, 0.5 mL HBS buffer was added and the contents were mixed (0.0125 mg/mL CFI). A 400 µL aliquot was transferred to a centrifugation filter and spun for 10 minutes at 10,000 rcf. The filtrate was transferred to the HPLC vial to measure the free drug by HPLC.

The release from the CFI preparations after freeze-thaw is consistent with the formation of ciprofloxacin nanocrystals which delay the release profile compared to the control CFI (FIG. 5). The T=0 release represents the amount of encapsulated drug prior to in vitro release, which was less than 1% for the control CFI and ranged from 6 to 9% for the nanocrystal formulations. All samples eventually released close to 100% of their encapsulated drug over the 4 hour time course in the assay. However, the rate of release for the control CFI was faster with close to 65% release after 50 min versus only 40% release for the samples containing nanocrystals after freeze-thaw.

Example 3

The IVR experiment was repeated for a CFI sample from batch ARA051 prepared in an identical manner to that in Example 2 and the results are shown in FIG. 6. In this case, the in vitro release profile of the CFI sample before and after freeze-thaw was reported. The CFI sample prior to freeze-thaw was similar to the control CFI whereas after freeze-thaw there was an increase in the T=0 release from 1% to ~12%, but then a delayed release profile from that point on consistent with the presence of ciprofloxacin nanocrystals.

Example 4

In this experiment two batches of CFI were used that contained both intraliposomal sucrose and extraliposomal sucrose. One batch of 50 mg/mL CFI, ARA054-01, had 50 mM sucrose internally (~17.1 mg/mL) while the second, ARA054-02, had 150 mM sucrose internally (~51.3 mg/mL). Both were formulated in 25 mM histidine and 300 mM sucrose (102.6 mg/mL) external to the liposomes, pH 6.0. The lots were diluted four-fold by adding 0.25 mL to 0.5 mL water and 0.25 mL 180 mg/mL sucrose to end up with an external sucrose concentration of ~70.7 mg/mL. None of the formulations contained any surfactant. Duplicate vials were prepared and one vial of each formulation was frozen in liquid nitrogen and then thawed to see if the formulations could withstand the freeze-thaw process and also if ciprofloxacin nanocrystals can be imputed to be present based on a slower IVR profile. Control CFI lot 0060 was also used.

The IVR assay was performed as described in Example 2 and the data are shown in FIG. 7. In the IVR assay, the control CFI sample was comparable to the two formulations prior to freeze-thaw. In the absence of surfactant, the amount of release at T=0 was relatively unchanged after freeze-thaw with close to 99% encapsulated. After 50 minutes incubation, the control samples had approximately 60 to 70% release versus 30% and 40% release for lot ARA054-01 and ARA054-02, respectively after freeze-thaw. Both profiles are consistent with the formation of ciprofloxacin nanocrystals causing a delayed release profile. Batch ARA054-01 had a slower release rate than batch ARA054-02, suggesting that the nanocrystals in the liposomes with lower internal sucrose had slower release than for the batch with higher internal sucrose.

Example 5

In this experiment one batch of CFI was used that contained 90 mg/mL sucrose only in the extraliposomal space. No surfactant was added to the liposomes. Duplicate vials were prepared. One vial was frozen in liquid nitrogen and then thawed. The other vial was not frozen and served as the control.

The IVR assay was performed as described in Example 2 and the data are shown in FIG. 8. In the IVR assay, the control CFI sample was comparable to that for previous control CFI formulations in the IVR assay (Examples 2 through 4). In the absence of surfactant, the amount of release at T=0 was unchanged after freeze-thaw with close to 99% remaining encapsulated. After 50 minutes incubation, the control sample had approximately 70% release versus 30% release for the sample after freeze-thaw. The IVR profile for the CFI sample after freeze-thaw is consistent with the formation of ciprofloxacin nanocrystals causing a delayed release profile.

Example 6

In this experiment one batch of CFI was used that contained 90 mg/mL sucrose only in the extraliposomal space. Instead of polysorbate 20, BRIJ 30 at various concentrations (0.01%, 0.05%, 0.1%, 0.2% and 0.3%) was added to the liposomes. One vial of each formulation was frozen in liquid nitrogen and then thawed. The CFI without BRIJ 30 and without being exposed to freeze-thaw was used as the control.

The IVR assay was performed as described in Example 2 and the data are shown in FIG. 9. In the IVR assay, the control CFI sample was comparable to that for previous control CFI formulations in the IVR assay (Examples 2 through 5). In the presence of surfactant, the amount of release at T=0 was increased with increasing amounts of surfactant. After 50 minutes incubation, the control sample had approximately 70% release versus 30 to 60% release for the samples containing BRIJ 30 after freeze-thaw. The IVR profiles for the CFI samples after freeze-thaw are consistent with the formation of ciprofloxacin nanocrystals causing a delayed release profile.

Example 7

In this experiment cryoTEM images were taken of a 12.5 mg/mL liposomal ciprofloxacin formulation after freeze-thaw that contained 90 mg/mL sucrose and 0.05% polysorbate 20 (FIG. 10), 0.1% polysorbate 20 (FIG. 11), or 0.2% polysorbate 20 (FIG. 12). After freeze-thaw, the CFI formulation containing 0.1% polysorbate 20 was nebulized using a PARI eFlow mesh nebulizer and the collected aerosol was also analyzed by CryoTEM imaging (FIG. 13). The lipid content was approximately 22.5 mg/mL implying a ratio of sucrose to lipid of approximately 4:1 on a weight basis. The cryoTEM was performed by diluting the sample from 12.5 mg/mL ciprofloxacin to 5 mg/mL and then freezing the samples in liquid ethane and vitrification. The sample with the least polysorbate 20 (FIG. 10) has more elongated liposomes with longer nanocrystals, while the sample with 0.1% polysorbate 20 (FIG. 11) has more circular liposomes with shorter nanocrystals and appeared unchanged after mesh nebulization (FIG. 13). The sample with 0.2% polysorbate 20 has more 'empty' liposomes consistent with the release of more encapsulated drug, thus increasing the portion of immediate release drug.

The instant invention is shown and described herein in a manner which is considered to be the most practical and preferred embodiments. It is recognized, however, that departures may be made therefrom which are within the scope of the invention and that obvious modifications will occur to one skilled in the art upon reading this disclosure.

While the instant invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

REFERENCES

Each of the following is incorporated by reference.
Abraham S A, Edwards K, Karlsson G, Hudon N, Mayer L D, Bally M B. 2004. An evaluation of transmembrane ion gradient-mediated encapsulation of topotecan within liposomes. *J Control Rel.* 96:449-461.
Bermudez L E, Motamedi N, Kolonoski P. Chee C, Baimukanova G, Bildfell R, Wang G, Phan L T, Young L S. The efficacy of clarithromycin and the bicyclolide EDP-420 against *Mycobacterium avium* in a mouse model of pulmonary infection. *J Infect Dis,* 197: 1506-10, 2008. PMID: 18422455
Bilton D, P Bruinenberg P, Otulana B. Inhaled liposomal ciprofloxacin hydrochloride significantly reduces sputum *Pseudomonas aeruginosa* density in CF and non-CF bronchiectasis. Presented at American Thoracic Society (ATS) International Conference, San Diego, Calif. *Am J Respir Crit Care Med* 179:A3214, 2009.
Bilton D, Bruinenberg P, Otulana B, Morishige R, Blanchard J, DeSoyza A, Serisier D. Inhaled liposomal ciprofloxacin hydrochloride significantly reduces sputum *Pseudomonas aeruginosa* density in CF and non-CF bronchiectasis. Presented at European Respiratory Society (ERS) Conference. Abstract 1362, 2009.
Bilton D, De Soyza A, Hayward C, Bruinenberg P. Effect of a 28-day course of two different doses of once a day liposomal ciprofloxacin for inhalation on sputum *Pseudomonas aeruginosa* density in non-CF bronchiectasis, Presented at American Thoracic Society (ATS) International Conference, New Orleans, La. *Am J Respir Crit Care Med* 181:A3191, 2010.
Bilton D, Serisier D J, DeSoyza A, Wolf R, Bruinenberg P. Multicenter, randomized, double-blind, placebo-controlled study (ORBIT 1) to evaluate the efficacy, safety, and tolerability of once daily ciprofloxacin for inhalation in the management of *Pseudomonas aeruginosa* infections in patients with non-cystic fibrosis bronchiectasis. Presented at European Respiratory Society Annual Congress, Amsterdam, The Netherlands. Abstract 1925, 2011.
Blanchard J D. Pulmonary drug delivery as a first response to bioterrorism. In: Dalby R N, Byron P R, Peart J, Suman J D, and Farr S J, eds., *Respiratory Drug Delivery X,* River Grove, I L: Davis Healthcare International, 2006, 73-82.
Bruinenberg P, Otulana B, Blanchard J, Morishige R, Cipolla D, Wilson J, Serisier D. The effect of once-a-day, inhaled liposomal ciprofloxacin hydrochloride for inhalation on bacterial density in cystic fibrosis patients with chronic *P. aeruginosa* infection. Presented at North American Cystic Fibrosis Conference, Orlando, Fla., 2008. *Ped Pulmon* 43 (Suppl 31):401, 2008.
Bruinenberg P, Otulana B, Blanchard J, Cipolla D, Wilson J, Serisier D. Pharmacokinetics and antibacterial activity of inhaled liposomal ciprofloxacin hydrochloride in healthy volunteers and in cystic fibrosis (C F) patients. Presented at 32nd European Cystic Fibrosis Conference, Brest, France. *J Cystic Fibrosis* 8 (Suppl 2):S49, 2009.
Bruinenberg P, Blanchard J, Cipolla D, Serisier D. Safety, tolerability and pharmacokinetics of novel liposomal ciprofloxacin formulations for inhalation in healthy volunteers and in non-cystic bronchiectasis patients. Presented at American Thoracic Society (ATS) International Conference, New Orleans, La. *Am J Respir Crit Care Med* 181:A3192, 2010.
Bruinenberg, P, Blanchard J D, Cipolla D C, Dayton F, Mudumba S, Gonda I. Inhaled liposomal ciprofloxacin: once a day management of respiratory infections. In: Dalby, R N, Byron P R, Peart J, Suman J D, Farr S J, Young P M, eds. *Respiratory Drug Delivery* 2010. River Grove, I L: Davis Healthcare International, 73-81, 2010.
Bruinenberg P, Serisier D, Blanchard J, Cipolla D, Gonda I. Effects and modulation of release rate of inhaled ciprofloxacin with liposomal formulations in healthy subjects and patients with bronchiectasis. Presented at European Respiratory Society Annual Congress, Barcelona, Spain. Abstract 1625, 2010.

Bruinenberg P, Serisier D, Cipolla D, Blanchard J. Safety, tolerability pharmacokinetics and antimicrobial activity of inhaled liposomal ciprofloxacin formulations in humans. Presented at North American Cystic Fibrosis Conference, Baltimore, Md. 45 (Suppl 33): Poster 377, 2010.

Bruinenberg P, Serisier D, Cipolla D, Blanchard J. Safety, tolerability, and pharmacokinetics of novel liposomal ciprofloxacin formulations in healthy volunteers (HV) and non-cystic fibrosis bronchiectasis (BE) patients. *J Cystic Fibrosis* 10 (Suppl 1): S29, 2011.

Carter G, Drummond D, Bermudez L E. Characterization of biofilm formation by *Mycobacterium avium* strains. *J Med Microbiol* 52: 747-52, 2003. PMID: 12909649

Chiu J, Nussbaum J, Bozzette S, Tilles J G, Young L S, Leedom J, Heseltine P N, McCutchan J A. Treatment of disseminated *Mycobacterium avium* complex infection in AIDS with amikacin, ethambutol and ciprofloxacin. *Ann Intern Med* 113: 358-61, 1990. PMID: 2382918

Cipolla D, Gonda I, and Chan H-K. (2013) Liposomal Formulations for Inhalation. *Ther. Deliv.* 4, 8, 1047-1072. doi: 10.4155/tde.13.71.

Cipolla D, Wu H, Eastman S, Redelmeier T, Gonda I and Chan H K. (2014) Development and Characterization of an In Vitro Release Assay for Liposomal Ciprofloxacin for Inhalation. *J. Pharm. Sci.* 103, 1, 314-327. doi: 10.1002/jps.23795.

Conley J, Yang H, Wilson T, Blasetti K, Di Ninno V, Schnell G, Wong J P. Aerosol delivery of liposome encapsulated ciprofloxacin: aerosol characterization and efficacy against *Francisella tuleransis* infection in mice. Antimicrob Agents Chemother 41: 1288-92, 1997. PMCID: PMC163901

Costerton J W, Lewandowski Z, Caldwell D E, Korber D R, Lappin-Scott H M., Microbial biofilms. Annu Rev Microbiol. 1995; 49:711-45.

Crowe J H, Crowe L M, Carpenter J F, Rudolph A S, Wistrom C A, Spargo B J, Anchordoguy T J. *Biochim Biophys Acta*. Interactions of sugars with membranes. 947 (1988) 367-384.

de Lalla F, Maserati R, Scarpellini P, Marone P, Nicolin R, Caccamo F, Rigoli R. Clarithromycin-ciprofloxacin-amikacin for therapy of *Mycobacterium avium-Mycobacterium intracellulare* bacteremia in patients with AIDS. Antimicrob Agents Chemother 36: 1567-9, 1992. PMCID: PMC191622

Di Ninno V L, Cherwonogrodzky J W, Wong J P. Liposome-encapsulated ciprofloxacin is effective in the protection and treatment of Balb/c mice against *Francisella tularensis*. J Infect Dis 168:793-794, 1993. PMID: 8354928

Drummond D C, Noble C O, Hayes M E, Park J W, Kirpotin D B. Pharmacokinetics and in vivo drug release rates in liposomal nanocarrier development. *J Pharm Sci.* 2008; 97:4696-4740.

Fiel S B. Aerosolized antibiotics in cystic fibrosis: current and future trends. Expert Rev Respir Med 2: 479-487, 2008. PMID: 20477211

Fitzsimmons S C. The changing epidemiology of cystic fibrosis. *J Pediatr.* 1993 January; 122(1):1-9.

Fowler S J, French J, Scranton N J, Foweraker J, Condliffe A, Haworth C S, Exley A R, Bilton D. Nontuberculous mycobacteria in bronchiectasis: prevalence and patient characteristics. Eur Respir J 28: 1204-10, 2006. PMID: 16807259

Gilbert P, Das J, Foley I., Biofilm susceptibility to antimicrobials. *Adv Dent Res.* 1997 April; 11(1):160-7.

Hamblin K A, Blanchard J D, Atkins H S. Efficacy of liposome-encapsulated ciprofloxacin against *Francisella tularensis* Schu S4 strain. Presented at Interscience Conference on Antimicrobial Agents and Chemotherapy (ICACC), Chicago, Ill., Poster F1-741, 2011.

Hamblin K A, Armstrong S J, Kay B, Barnes K B, Davies C, Wong J P, Blanchard J D, Harding S V, Simpson A J H, Atkins H S. Liposome-encapsulation of ciprofloxacin improves protection against highly resistant *Francisella tularensis* Schu S4 strain. Antimicrob Agents Chemother 2014 (In press) PMID: 24637682.

Hodson M, Shah P L, DNase trials in cystic fibrosis. *Respiration* 1995; 62, Suppl 1: 29-32.

Inderlied C, Kolonoski P, Wu M, Young L. Amikacin, ciprofloxacin, and imipenem treatment for disseminated *Mycobacterium avium* complex infection of beige mice. Antimicrob Agents Chemother 33: 176-80, 1989. PMCID: PMC171452

Inderlied C B, Kemper C A, Bermudez L E. The *Mycobacterium avium* complex. Clin Micro Rev 6: 266-310, 1993. PMCID: PMC358286

Islam M S, Richards J P, Ojha A K. Targeting drug tolerance in mycobacteria: a perspective from mycobacterial biofilms. Expert Rev Anti Infect Ther. 10(9): 1055-1066 (2012).

Jordao L, Bleck C K, Mayorga L, Griffths G, Anes E. On the killing of mycobacteria by macrophages. Cell Microbiol 10: 529-48, 2008. PMID: 17986264

Izutsu K I, Yomota C, Kawanishi T. Stabilization of liposomes in frozen solutions through control of osmotic flow and internal solution freezing by trehalose. *J Pharm Sci.* 100, 7, (2011) 2935-2944.

Lasic D D, Frederick P M, Stuart M C A, Barenholz Y, McIntosh T J. 1992. Gelation of liposome interior: A novel method for drug encapsulation. *FEBS Lett.* 312: 255-258.

Lasic D D, Ceh B, Stuart M C A, Guo L, Frederik P M, Barenholz Y. 1995. Transmembrane gradient driven phase transitions within vesicles: lessons for drug delivery. *Biochim Biophys Acta.* 1239, 145-156.

Li X, Hirsh D J, Cabral-Lilly D, Zirkel A, Gruner S M, Janoff A S, Perkins W R. Doxorubicin physical state in solution and inside liposomes loaded via a pH gradient. *Biochim Biophys Acta.* 1998 Dec. 9; 1415(1):23-40.PMID: 9858673.

Lode H, Bomer K, Koeppe P, Schaberg T., Azithromycin—review of key chemical, pharmacokinetic and microbiological features. *J Antimicrob Chemother.* 1996; 37, Suppl C: 1-8

Majumdar S, Flasher D, Friend D S, Nassos P, Yajko D, Hadley W K, Düzgüneş N. Efficacies of liposome-encapsulated streptomycin and ciprofloxacin against *Mycobacterium avium-M. intracellulare* complex infections in human peripheral blood monocytes/macrophages. Antimicrob Agents Chemother 36: 2808-15, 1992. PMCID: PMC245550.

McNabe M, Tennant R, Danelishvili L, Young L, Bermudez L E. *Mycobacterium avium* ssp. *hominissuis* biofilm is composed of distinct phenotypes and influenced by the presence of antimicrobials. Clin Microbiol Infect 17(5) 697-703 (2012). PMID: 20636426

Meers P, Neville M, Malinin V, Scotto A W, Sardaryan G, Kurumunda R, Mackinson C, James G, Fisher S, Perkins W R. Biofilm penetration, triggered release and in vivo activity of inhaled liposomal amikacin in chronic Pseudomanas *aeruginosa* lung infections, J Antimicrob Chemother, 61: 859-68, 2008. PMID: 18305202

Moss R B., Administration of aerosolized antibiotics in cystic fibrosis patients. *Chest.* 2001 September; 120(3 Suppl):107S-113S.

Oh Y K, Nix D E, Straubinger R M. Formulation and efficacy of liposome-encapsulated antibiotics for therapy of intracellular *Mycobacterium avium* infection. Antimicrob Agents Chemother 39: 2104-11, 1995. PMCID: PMC162889

Niven R N and Schreier H. Nebulization of Liposomes: I. Effects of Lipid Composition. *Pharm Res.* 1990; 7:1127-1133.

Polonio R E Mermel L A, Paquette G E, Sperry J F., Eradication of biofilm-forming *Staphylococcus epidermidis* (RP62A) by a combination of sodium salicylate and vancomycin. *Antimicrob Agents Chemother.* 2001 November; 45(11):3262-6.

Prevots R D, Shaw P A, Strickland D, Jackson L A, Raebel M A, Blosky M A, Montes de Oca R, Shea Y R, Seitz A E, Holland S M, Olivier, K N. Nontuberculosis mycobacterial lung disease prevalence at four integrated health care delivery systems. Am J Respir Crit Care Med 182: 970-976, 2010 PMID: 20538958.

Serisier D J, Bilton D, De Soyza A, Thompson P J, Kolbe J, Greville H W, Cipolla D, Bruinenberg P, and Gonda I. (2013) Inhaled, Dual-Release Liposomal Ciprofloxacin in Non-Cystic Fibrosis Bronchiectasis (ORBIT-2)—a Randomised, Double-Blind, Placebo-Controlled Trial. Thorax. Vol. 68, No. 9, pp. 812-817 doi: 10.1136/thoraxjnl-2013-203207.

Schroeder S A Gaughan D M, Swift M., Protection against bronchial asthma by CFTR delta F508 mutation: a heterozygote advantage in cystic fibrosis. *Nat Med.* 1995 July; 1(7):703-5.

Shafran S D, Singer J, Zarowny D P, Phillips P, Salit I, Walmsley S L, Fong I W, Gill M J, Rachlis A R, Lalonde R G, Fanning M M, Tsoukas C M. A comparison of two regimens for the treatment of *Mycobacterium avium* complex bacteremia in AIDS, rifampin, ethambutol, and clarithromycin, versus rifampin, ethambutol, clofazimine and ciprofloxacin. N Engl J Med 335: 377-83, 1996. PMID: 8676931

Siow L F, Rades T, Lim M H. Characterizing the freezing behavior of liposomes as a tool to understand the cryopreservation procedures. *Cryobiology.* 55 (2007) 210-221.

Siow L F, Rades T, Lim M H. Cryo-responses of two types of large unilamellar vesicles in the presence of non-permeable or permeable cryoprotecting agents. *Cryobiology.* 57 (2008) 276-285.

Smith A L, Ramsey B W, Hedges D L, Hack B, Williams-Warren J, Weber A, Gore E J, Redding G J. Safety of aerosol tobramycin administration for 3 months to patients with cystic fibrosis. *Ped Pulmonol.* 1989; 7(4): 265-271.

Stark B, Pabst G, Prassl R. Long-term stability of sterically stabilized liposomes by freezing and freeze-drying: Effects of cryoprotectants on structure. *Eur J Pharm Sci.* 41(2010) 546-555.

Strauss G and Hauser H. PNAS. Stabilization of lipid bilayer vesicles by sucrose during freezing. *PNAS.* 83, 2422-2426, 1986.

Weber A, Smith A, Williams-Warren J, Ramsey B, Covert D S., Nebulizer delivery of tobramycin to the lower respiratory tract. *Pediatr Pulmonol.* 1994 May; 17(5):331-9.

Wong J P, Yang H, Blasetti K L, Schnell G, Conley J, Schofield L N. Liposome delivery of ciprofloxacin against intracellular *Francisella tularensis* infection. J Control Release 92: 265-73, 2003. PMID: 14568408

Wong J P, Schnell G, Simpson M, Saravolac E. Effects of liposome-encapsulated ciprofloxacin on phagocytosis, nitric oxide, and intracellular killing of *Staphylococcus aureus* by murine macrophages. Artific Cells Blood Substit Immobil Biotechnol 28: 415-28, 2000. PMID: 11009114

Wolter J, Seeney S, Bell S, Bowler S, Masel P, McCormack J., Effect of long term treatment with azithromycin on disease parameters in cystic fibrosis: a randomised trial. *Thorax.* 2002; 57: 212-216.

Wolkers W F, Oldenhof H, Tablin F, Crowe J H. 2004. Preservation of dried liposomes in the presence of sugar and phosphate. *Biochim. Biophys. Acta* 1661, 125-134.

Yamazaki Y, Danelishvili L, Wu M, Hidaka E, Katsuyama T, Stang B, Petrofsky M, Bildfell R, Bermudez L. The ability to form biofilm influences *Mycobacterium avium* invasion and translocation of bronchial epithelial cells. Cell Microbiol 8: 806-14, 2006. PMID: 16611229

Yeager H, Raleigh J W. Pulmonary disease due to *Mycobacterium intracellulare*. Am Rev Resp Dis 108: 547-52, 1973. PMID: 4745250

Zielenski J, Tsui L C., Cystic fibrosis: genotypic and phenotypic variations. *Annual Rev Genet.* 1995; 29:777-807.

Zhigaltsev I V, Maurer N, Edwards K, Karlsson G, Cullis P R. 2006. Formation of drug-arylsulfonate complexes inside liposomes: A novel approach to improve drug retention. *J Control Rel.* 110: 378-386.

What is claimed is:

1. A formulation, comprising:

liposomes wherein the liposomes comprise:

a lipid bilayer comprised of sucrose and a phosphatidylcholine-enriched phospholipids present at a ratio between 1:10 to 10:1 (w/w);

a sucrose cryopreservative;

a polysorbate 20 in an amount of between 0.01% to 1%; and nanocrystals of ciprofloxacin surrounded by the lipid bilayer wherein the nanocrystals have dimensions of 200 nm or less.

2. The formulation of claim 1, further comprising:

a pharmaceutically acceptable carrier.

3. The formulation of claim 2, wherein the ciprofloxacin is:

dissolved in the carrier.

4. The formulation of claim 1, further comprising:

a liquid form of a pharmaceutically active drug in which the liposomes are dispersed.

5. The formulation of claim 4, wherein the drug in liquid form is an anti-infective drug.

6. The formulation of claim 5, wherein the anti-infective drug is selected from the group consisting of a quinolone, a sulfonamide, an aminoglycoside, a tetracycline, para-aminobenzoic acid, a diaminopyrimidine, a beta-lactam, a beta-lactam and a beta-lactamase inhibitor, chloramphenicol, a macrolide, lincomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, polyene antifungal, flucytosine, imidazole, triazole, griseofulvin, terconazole, butoconazole ciclopirax, ciclopirox olamine, haloprogin, tolnaftate, naftifine, terbinafine and combinations thereof;

wherein the lipid bilayer is comprised of a lipid selected from the group consisting of fatty acids; lysolipids; sphingolipids; sphingomyelin; glycolipids; glucolipids;

glycosphingolipids; palmitic acid; stearic acid; arachidonic acid; oleic acid; lipids bearing sulfonated mono-, di-, oligo- or polysaccharides; lipids with ether and ester-linked fatty acids, polymerized lipids, diacetyl phosphate, stearylamine, cardiolipin, phospholipids, synthetic phospholipids with asymmetric acyl chains; and lipids bearing a covalently bound polymer; and wherein the liposome comprises a phospholipid selected from the group consisting of phosphatidylcholines, lysophosphatidylcholines, phosphatidylethanolamines, phosphatidylinositols, phosphatidylglycerols, phosphatidic acid, phosphatidylserines, and mixtures thereof; wherein said phospholipid is provided in admixtures with a modifying agent selected from the group consisting of cholesterols, stearyl amines, stearic acid, tocopherols, and mixtures thereof; and wherein the liposomes are unilamellar or multilamellar.

7. The formulation of claim 6,
wherein the nanocrystals have dimensions of 100 nanometers or less.

8. The formulation of claim 7,
wherein the nanocrystals have a dimension of 50 nanometers to 75 nanometers;
wherein 90% or more of the liposomes maintain structural integrity when liposome temperature is decreased to a reduced temperature in a range of −20° C. to −80° C.; and
stored at the reduced temperature for a period of one week or more at the reduced temperature; and
thawed by increasing the temperature to a temperature in a range of 5° C. to 30° C.

9. The formulations as claimed in claim 8, wherein the formulation is aerosolized into particles having an aerodynamic diameter in a range of from 1 micron to 12 microns and liposomes having a diameter in a range of 20 nanometers to 1 micron, wherein at least 90% of the liposomes are comprised of a composition which allow the liposomes to maintain structural integrity after aerosolization.

10. A liposome formulation produced by a process comprising the steps of:
providing a solution of ciprofloxacin;
forming spherical lipid bilayers around the ciprofloxacin solution thereby encapsulating the solution in liposomes wherein the lipid bilayer is comprised of sucrose and a phosphatidylcholine-enriched phospholipids present at a ratio between 1:10 to 10:1 (w/w), and polysorbate 20 in an amount of between 0.01% to 1%;
freezing the liposomes;
maintaining the liposomes frozen over a period of time;
raising the temperature of the liposomes to a temperature above a freezing point of the solution to a temperature whereby nanocrystals of ciprofloxacin are formed wherein the nanocrystals have dimensions of 100 nanometers to 50 nanometers.

11. The formulation of claim 10, wherein freezing is to a temperature of from −20° C. to −80° C., and the freezing is maintained over a period of time of one week or more.

12. A method of treatment, comprising:
aerosolizing a formulation to create aerosolized particles having a aerodynamic diameter in a range of from 2 microns to 12 microns;
wherein the formulation comprises:
a pharmaceutically acceptable carrier;
ciprofloxacin; and
liposomes wherein the liposomes comprise:
a lipid bilayer comprised of sucrose and a phosphatidylcholine-enriched phospholipids present at a ratio between 1:10 to 10:1 (w/w);
a polysorbate 20 in an amount of between 0.01% to 1%;
nanocrystals of the ciprofloxacin surrounded by the lipid bilayer wherein the nanocrystals have dimensions of 200 nm or less;
wherein the liposomes are dispersed in a liquid form of a pharmaceutically active drug; and
inhaling the aerosolized particles.

13. The method of claim 4, wherein the pharmaceutically active drug in liquid form is an anti-infective drug selected from the group consisting of a quinolone, a sulfonamide, an aminoglycoside, a tetracycline, para-aminobenzoic acid, a diaminopyrimidine, a beta-lactam, a beta-lactam and a beta-lactamase inhibitor, chloramphenicol, a macrolide, lincomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, polyene antifungal, flucytosine, imidazole, triazole, griseofulvin, terconazole, butoconazole ciclopirax, ciclopirox olamine, haloprogin, tolnaftate, naftifine, terbinafine and combinations thereof;

wherein the lipid bilayer is comprised of a lipid selected from the group consisting of fatty acids; lysolipids; sphingolipids; sphingomyelin; glycolipids; glucolipids; glycosphingolipids; palmitic acid; stearic acid; arachidonic acid; oleic acid; lipids bearing sulfonated mono-, di-, oligo- or polysaccharides; lipids with ether and ester-linked fatty acids, polymerized lipids, diacetyl phosphate, stearylamine, cardiolipin, phospholipids, synthetic phospholipids with asymmetric acyl chains; and lipids bearing a covalently bound polymer; and wherein the liposome comprises a phospholipid selected from the group consisting of phosphatidylcholines, lysophosphatidylcholines, phosphatidylethanolamines, phosphatidylinositols, phosphatidylglycerols, phosphatidic acid, phosphatidylserines, and mixtures thereof; wherein said phospholipid is provided in admixtures with a modifying agent selected from the group consisting of cholesterols, stearyl amines, stearic acid, tocopherols, and mixtures thereof; and wherein the liposomes are unilamellar or multilamellar.

14. The method of claim 4,
wherein the nanocrystals have dimensions of 100 nanometers or less and wherein;
the pharmaceutically active drug wherein in liquid form is ciprofloxacin; and
the aerosol is inhaled into a human patient's lungs.

15. A formulation, comprising:
a pharmaceutically acceptable carrier;
ciprofloxacin dissolved in the carrier;
liposomes dispersed in the carrier, wherein the liposomes comprise:
a lipid bilayer comprised of sucrose and a phosphatidylcholine-enriched phospholipids present at a ratio between 1:10 to 10:1 (w/w);
polysorbate 20 in an amount of between 0.01% to 1%; and
nanocrystals of ciprofloxacin having a dimension of 50 nanometers to 75 nanometers wherein the nanocrystals are surrounded by a solution of ciprofloxacin which is surrounded by the lipid bilayer;
wherein the lipid bilayer is comprised of polyol and phosphatidylcholine-enriched phospholipids present at a ratio between 1:1 and 5:1 (w/w).

* * * * *